(12) United States Patent
Bystricky et al.

(10) Patent No.: US 9,611,486 B2
(45) Date of Patent: Apr. 4, 2017

(54) CONSTRUCTS AND METHOD FOR REGULATING GENE EXPRESSION OR FOR DETECTING AND CONTROLLING A DNA LOCUS IN EUKARYOTES

(75) Inventors: Kerstin Bystricky, Vigoulet-Auzil (FR); Franck Gallardo, Bressols (FR); David Lane, Toulouse (FR); Nelly Dubarry, Oxford (GB)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/006,743

(22) PCT Filed: Mar. 23, 2012

(86) PCT No.: PCT/EP2012/055258
§ 371 (c)(1),
(2), (4) Date: Oct. 22, 2013

(87) PCT Pub. No.: WO2012/127047
PCT Pub. Date: Sep. 27, 2012

(65) Prior Publication Data
US 2014/0045262 A1    Feb. 13, 2014

(30) Foreign Application Priority Data
Mar. 24, 2011    (FR) ..................... 11 52473

(51) Int. Cl.
| | | |
|---|---|---|
| C12N 15/63 | (2006.01) | |
| C12N 15/82 | (2006.01) | |
| C12N 15/85 | (2006.01) | |
| C07K 14/21 | (2006.01) | |
| C12N 15/81 | (2006.01) | |
| C12N 5/07 | (2010.01) | |
| C12N 5/071 | (2010.01) | |
| C12N 5/10 | (2006.01) | |

(52) U.S. Cl.
CPC .............. *C12N 15/85* (2013.01); *C07K 14/21* (2013.01); *C12N 15/81* (2013.01); *C12N 15/8212* (2013.01); *C12N 15/8216* (2013.01); *C07K 2319/80* (2013.01)

(58) Field of Classification Search
None
See application file for complete search history.

(56) References Cited

PUBLICATIONS

Edelstein et al., "Gene therapy clinical trials worldwide 1989-2004—an overview" 6 The Journal of Gene Medicine 597-602 (2004).*
Edelstein et al., "Gene therapy clinical trials worldwide 1989-2004—an overview" 6 Journal of Gene Medicine 597-602 (2004).*
Verma et al., "Gene Therapy: Twenty-First Century Medicine" 74 Annual Review of Biochemistry 711-738 (2005).*
Batard, P., et al., "Transfer of high copy number plasmid into mammalian cells by calcium phosphate transfection", "Gene", May 30, 2001, pp. 61-68, vol. 270, No. 1-2.
Belli, G., et al., "An activator/repressor dual system allows tight tetracycline-regulated gene expression in budding yeast", "Nucleic Acids Research", Feb. 15, 1998, pp. 942-947, vol. 26, No. 4.
Belmont, A., et al., "In vivo visualization of chromosomes using lac operator-repressor binding", "Trends in Cell Biology", Mar. 1998, pp. 121-124, vol. 8, No. 3.
Belmont, A., "Visualizing chromosome dynamics with GFP", "Trends in Cell Biology", Jun. 2001, pp. 250-257, vol. 11, No. 6.
Bystricky, K., et al., "Chromosome looping in yeast: telomere pairing and coordinated movement reflect anchoring efficiency and territorial organization", "The Journal of Cell Biology", Jan. 31, 2005, pp. 375-387, vol. 168, No. 3.
Bystricky, K., et al., "Regulation of Nuclear Positioning and Dynamics of the Silent Mating Type Loci by the Yeast Ku70/Ku80 Complex", "Molecular and Cellular Biology", Dec. 1, 2008, pp. 835-848, vol. 29, No. 3.
Database EMBL [Online], "GQ0011.TB_K09 GQ001: Male Strobili developmental sequence Picea glauca cDNA clone GQ0011_K09 3, mRNA sequence", Database accession No. CK442097, Jan. 9, 2004, Pos. 387-399, XP002663655, extracted from EBI accession No. EMBL: CK442097.
Database EMBL [Online], "104_409_10906520_116_32497_020 Sorghum methylation-filtered library (LibID: 104) Sorghum bicolor genomic clone 10906520, genomic survey sequence.", Database accession No. CL191061, Jan. 7, 2004, Pos. 320-332, XP002663654, extracted from EBI accession No. EMBL: CL191061.
Davis, M., et al., "Recognition of the P1 plasmid centromere analog involves binding of the ParB protein and is modified by a specific host factor", "The EMBO Journal", Jun. 1988, pp. 1881-1888, vol. 7, No. 6.
Dubarry, N., et al., "ParABS Systems of the Four Replicons of Burkholderia cenocepacia: New Chromosome Centromeres Confer Partition Specificity", "Journal of Bacteriology", Feb. 2006, pp. 1489-1496, vol. 188, No. 4.
Gari, E., et al., "A Set of Vectors with a Tetracycline-Regulatable Promoter System for Modulated Gene Expression in *Saccharomyces cerevisiae*", "Yeast", Jul. 1997, pp. 837-848, vol. 13, No. 9.
Gietz, R., et al., "Applications of High Efficiency Lithium Acetate Transformation of Intact Yeast Cells using Single-Stranded Nucleic Acids as Carrier", "Yeast", Apr. 1991, pp. 253-263, vol. 7, No. 3.
Golovanov, A., et al., "ParG, a protein required for active partition of bacterial plasmids, has a dimeric ribbonhelixhelix structure", "Molecular Microbiology", Nov. 2003, pp. 1141-1153, vol. 50, No. 4.

(Continued)

*Primary Examiner* — Nancy J Leith
(74) *Attorney, Agent, or Firm* — Hultquist, PLLC; Mary B. Grant

(57) ABSTRACT

The present invention concerns constructs based on sequences derived from the partitioning system of plasmid and chromosomal DNA of bacteria, such as eukaryotic expression vectors, fusion proteins and polynucleotides encoding the same and also eukaryotic cells transformed with or expressing such constructs. The present invention also concerns the use thereof in the regulation of gene expression and/or in the detection and control of the dynamics, localization or metabolism of genomic DNA loci of interest in eukaryotic cells.

12 Claims, 8 Drawing Sheets

(56) References Cited

PUBLICATIONS

Joffe, B., et al., "Differentiation and large scale spatial organization of the genome", "Current Opinion in Genetics & Development", Jun. 17, 2010, pp. 562-569, vol. 20, No. 5.

Li, Y., et al., "The P1 plasmid is segregated to daughter cells by a 'capture and ejection' mechanism coordinated with *Escherichia coli* cell division", "Molecular Microbiology", Oct. 2002, pp. 63-74, vol. 46, No. 1.

Lin, D., et al., "Identification and Characterization of a Bacterial Chromosome Partitioning Site", "Cell", Mar. 6, 1998, pp. 675-685, vol. 92, No. 5.

Livny, J., et al., "Distribution of Centromere-Like parS Sites in Bacteria: Insights from Comparative Genomics", "Journal of Bacteriology", Sep. 28, 2007, pp. 8693-8703, vol. 189, No. 23.

Lynch, A., et al., "SopB protein-mediated silencing of genes linked to the sopC locus of *Escherichia coli* F plasmid", "Proc. Natl. Acad. Sci. USA", Mar. 14, 1995, pp. 1896-1900, vol. 92, No. 6.

Michaelis, C., et al., "Cohesins: Chromosomal Proteins that Prevent Premature Separation of Sister Chromatids", "Cell", Oct. 3, 1997, pp. 35-45, vol. 91, No. 1.

Murray, H., et al., "The bacterial chromosome segregation protein Spo0J spreads along DNA from parS nucleation sites", "Molecular Microbiology", Sep. 2006, pp. 1352-1361, vol. 61, No. 5.

Ozawa, T., et al., "Rapid isolation of viral integration site reveals frequent integration of HTLV-1 into expressed loci", "J Hum Genet", Feb. 26, 2004, pp. 154-165, vol. 49, No. 3.

Straight, A., et al., "GFP tagging of budding yeast chromosomes reveals that proteinprotein interactions can mediate sister chromatid cohesion", "Current Biology", Dec. 1, 1996, pp. 1599-1608, vol. 6, No. 12.

Surtees, J., et al., "P1 ParB Domain Structure Includes Two Independent Multimerization Domains", "Journal of Bacteriology", Oct. 1999, pp. 5898-5908, vol. 181, No. 19.

Therizols, P., et al., "Chromosome arm length and nuclear constraints determine the dynamic relationship of yeast subtelomeres", "Proc. Natl. Acad. Sci. USA", pp. 2025-2030, vol. 107, No. 5, Feb. 2, 2010.

Dillon, S., et al., "Bacterial nucleoid-associated proteins, nucleoid structure and gene expression", "Nature Reviews Microbiology", Feb. 8, 2010, pp. 185-195, vol. 8.

Rodionov, O., et al., "Silencing of Genes Flanking the P1 Plasmid Centromere", "Science", Jan. 22, 1999, pp. 546-549, vol. 283.

* cited by examiner

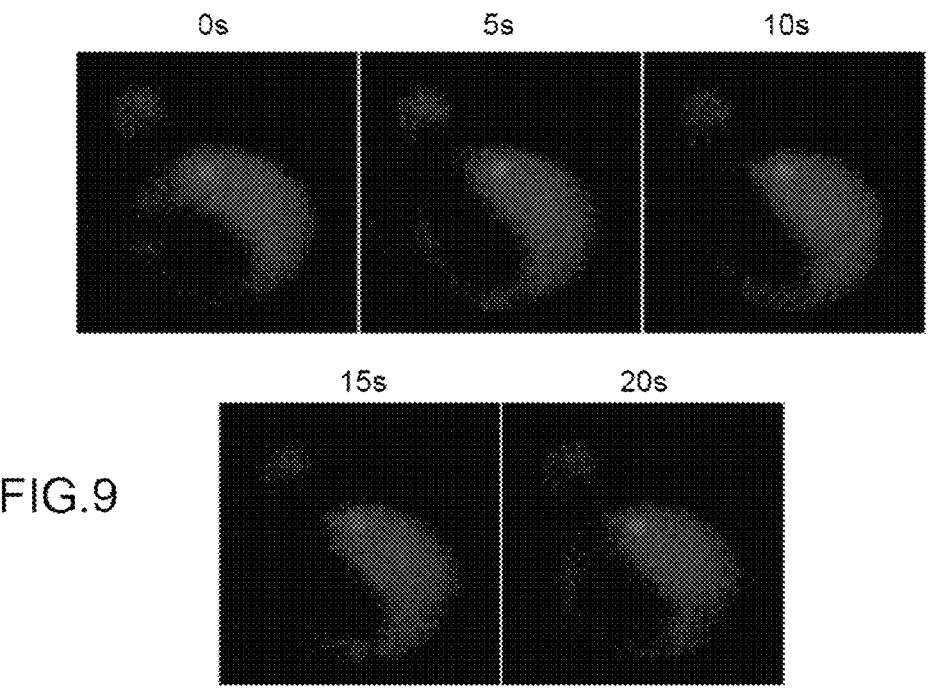
FIG.9
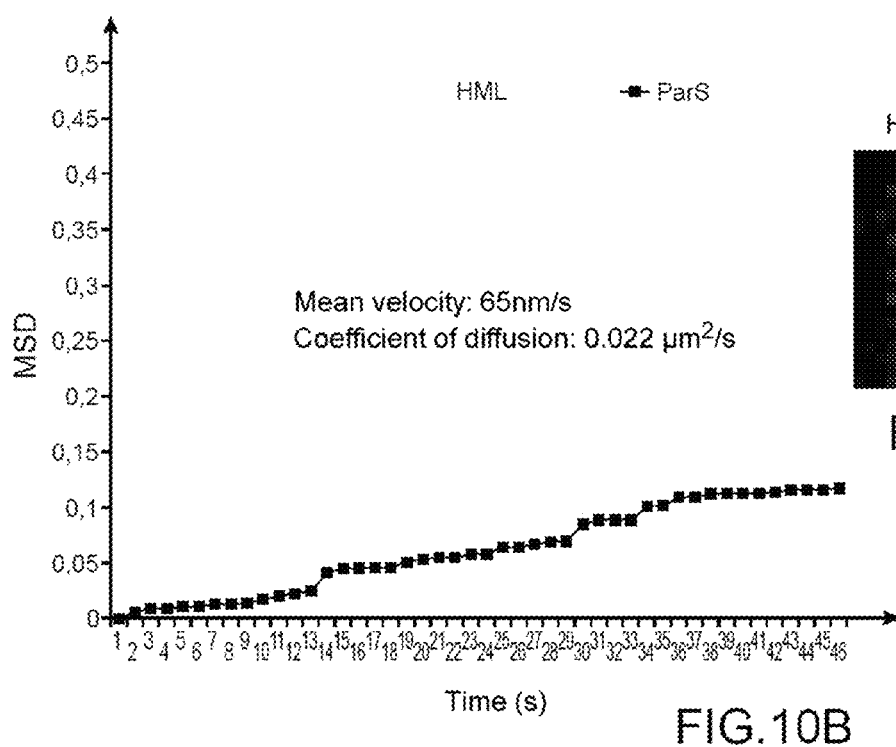
FIG.10A
FIG.10B

CONSTRUCTS AND METHOD FOR REGULATING GENE EXPRESSION OR FOR DETECTING AND CONTROLLING A DNA LOCUS IN EUKARYOTES

CROSS-REFERENCE TO RELATED APPLICATIONS

This application is a U.S. national phase under the provisions of 35 U.S.C. §371 of International Patent Application No. PCT/EP12/55258 filed Mar. 23, 2012, which in turn claims priority of French Patent Application No. 1152473 filed Mar. 24, 2011. The disclosures of such international patent application and French priority patent application are hereby incorporated herein by reference in their respective entireties, for all purposes.

TECHNICAL FIELD

The present invention generally concerns the field of biotechnologies and in particular the field of instruments useful in biotechnology.

More particularly the present invention proposes the use of sequences derived from the partitioning system of bacterial plasmid and chromosomal DNA for the regulation of gene expression in eukaryotic cells and in particular living eukaryotic cells and/or for the detection and control of genomic DNA loci of interest in said cells.

The present invention therefore concerns the constructs used in these regulation, detection and control methods such as eukaryotic expression vectors, fusion proteins and polynucleotides encoding the same, and eukaryotic cells transformed with or expressing such constructs.

The present invention also concerns a method for regulating gene expression in a eukaryotic cell and a method for detecting and controlling a genomic DNA locus of interest in a eukaryotic cell.

STATE OF THE PRIOR ART

The visualisation of genomic DNA loci in vivo is typically obtained using a two-component system involving a DNA target sequence (called operator) which is recognised and specifically bound by a protein (called repressor) (Belmont, 2001; Belmont & Straight, 1998; Straight et al, 1996). This system known as FROS (Fluorescent Repressor Operator System) has been routinely used to detect the position of DNA regions in the living cells of bacteria and as far as mammalian cells.

At the present time only two systems of Operator/Repressor type i.e. the LacO/LacI and TetO/TetR systems are available for in vivo imaging (Bystricky et al, 2005; Michaelis et al, 1997; Therizols et al, 2010) in eukaryotes.

One of the disadvantages of these systems lies in the size and repeating nature of the operator sequences. This type of operator is effectively composed of more than two hundred repeats of a bacterial operator sequence. On this account, in its current version, the LacO operator includes more than 10 kb DNA.

Even if this technique has allowed the visualisation of DNA regions in vivo, the inserting of these enormous sequences may modify the behaviour of the chromatin fibre. In addition, the stretching and compacting of chromosomal regions of this size may distort the conducting of dynamic studies such as the tracking of fluorescent particles over time.

On this account, the study in living cells of the architecture and dynamics of chromosomes is largely limited by the size of the operator sequence itself. Techniques involving the detection of short non-repeated DNA sequences have not yet been developed for eukaryotes.

There is therefore a true need for systems and constructs allowing the study in eukaryotic cells, and in particular living eukaryotic cells, of the architecture and dynamics of chromosomes. The inventors have set themselves the objective of identifying such systems and such constructs.

The partitioning or segregation of chromosomes during mitosis in bacteria occurs via a system comprising three elements: a short sequence, called ParS, a ParB protein which binds to ParS and a second protein ParA having ATPase activity which mobilises the ParB-ParS complexes (Lin & Grossman, 1998). On the chromosomes, ParS is typically present in a few copies distributed within the region of the origin of replication (Livny et al, 2007). ParB binds specifically at a binding sequence present at the ParS sequence. Once bound, ParB is capable of recruiting other copies of itself by means of its N-terminal domain. In addition, ParB spreads over DNA in the vicinity of the binding site in bi-directional manner (Murray et al, 2006; Lynch & Wang, 1995). Most bacterial species contain a single chromosome and parS sites having an identical or almost identical sequence.

In contrast, the bacterium *Burkholderia cenocepacia* (Bcc) contains three chromosomes and a plasmid with a low number of copies which are independently partitioned by specific partitioning systems called Par-c1 (partition system of chromosome 1), Par-c2 (partitioning system of chromosome 2), Par-c3 (partitioning system of chromosome 3) and Par-p1 (partitioning system of the plasmid). Each of these four replicons carries a few copies of a parS of specific sequence distributed over about 1 kb (Dubarry et al, 2006). In this article, different plasmid constructs were prepared such as plasmids derived from pDAG203 in which the parS sequence derived from any of the chromosomes or the plasmid of Bcc has been inserted. Said plasmids were used to transform the bacterium *Escherichia coli* (*E. coli*). However, these plasmids do not form eukaryotic vectors such as defined below.

The partitioning system of plasmid and chromosomal DNA in bacteria and in particular the system based on the centromere ParS and the protein ParB which binds thereto, has only been used in bacteria. More specifically, the work known to date has focused on the ParB protein of the P1 plasmid of *E. coli*. Yet, this protein has the disadvantage of binding to the binding sites present at the ParS sequence solely in the presence of a host factor called IHF (Integration Host Factor) (Li & Austin, 2002). This dependency on IHF has largely limited interest in this system. The work described by Li & Austin (2002) uses fusion proteins corresponding to all or part of the ParB protein of the P1 plasmid of *E. coli*, fused to the C-terminal end of the Green Fluorescent Protein (GFP). These fusion proteins were produced using the pDSW209 plasmid modified to comprise a nucleotide sequence coding for these fusion proteins and inserted in bacterial strains such as W3110 and N100.

Similarly, in the article by Surtees & Funnell (1999), the ParB protein of the P1 plasmid of *E. coli* is used, using the double-hybrid technique, to detect and study the interactions between the components of ParB and their dimerisation in particular. In the constructs formed, all or part of the ParB protein of the P1 plasmid of *E. coli* is fused to the eukaryotic transcription factor Gal4. It is this factor which brings ParB close to a reporter gene allowing visualisation of the expression thereof by means of the interaction of the ParB protein fused to Gal4 with the partner it is sought to characterize. To summarise, the association with DNA of the fusion protein such as described in Surtees & Funnell (1999) is due to Gal4 and not to ParB of the P1 plasmid of *E. coli* since the latter alone is incapable of such association.

DISCLOSURE OF THE INVENTION

With the present invention it is possible to solve the technical problems such as previously defined and to reach the objective set by the inventors.

The work conducted by the inventors has allowed a general method to be developed with which to visualise and study the dynamics of chromatin loci in vivo by applying the Bcc partitioning system for use thereof in eukaryotic cells.

One of the advantages of this method lies in the largely reduced size of the genomic insertion (1 kb) compared with the other systems used (>10 kb) and in the low number of repeats of the binding sequence (also called recognition sequence herein). On this account, all the methods used to preserve the size of the operator sequences in the state of the art become obsolete in the system and methods of the present invention.

In noteworthy manner, these constructs can be used not only to detect and control genomic loci of interest and to visualise an unknown step in the metabolism of DNA such as degradation during double-strand breaks, but also to regulate and control the expression of genes in eukaryotes.

Finally, the teaching of the work by the inventors using elements of the DNA partitioning system of the Bcc bacterium can be generalised to the elements of any DNA partitioning system of any bacterium provided that, in this bacterium, the DNA binding protein belonging to the DNA partitioning system is capable, at a recognition site, of binding the DNA without requiring another factor such as an organic factor and in particular a protein factor and, advantageously, is also capable of recruiting other copies of itself.

The present invention firstly concerns a eukaryotic expression vector comprising a nucleotide sequence coding for a particular fusion protein.

By « eukaryotic expression vector» is meant a vector adapted for the expression, in a eukaryotic cell, of at least one polypeptide encoded by a nucleotide sequence contained in this vector. Said vector is useful in particular for transforming a host eukaryotic body and for expressing therein a fusion protein such as defined below.

The eukaryotic expression vector of the present invention, in addition to the nucleotide sequence encoding a fusion protein, comprises one or more elements which allow the expression i.e. the transcription and translation of this nucleotide sequence.

The eukaryotic expression vector of the present invention is advantageously chosen from among a plasmid, cosmid, bacteriophage and a virus such as a baculovirus.

In particular, the vector of the invention is an autonomously replicating vector comprising elements allowing the maintaining and replication thereof in the host organism like an origin of replication. In addition, the vector may comprise elements allowing its selection in the host organism. These elements are also known as « selectable markers» . Said expression vectors are well known to persons skilled in the art and are widely described in the literature.

A eukaryotic expression vector differs from a prokaryotic expression vector through the presence, on the eukaryotic vector, of at least one element chosen from among an origin of replication of eukaryotic type, a selectable marker of eukaryotic type, a promoter of eukaryotic type, an amplifier also known as an enhancer, a 3' UTR signal (UnTranslated Region), an IRES signal (Internal Ribosome Entry Site) and a eukaryotic transcription terminating signal comprising a cleavage site and/or a polyA signal (polyadenylation signal). The eukaryotic expression vector of the invention may comprise 2, 3, 4, 5, 6 or 7 elements listed above and typically all these elements.

By « selectable marker of eukaryotic type» is meant a marker chosen from among a gene of the metabolism to be used with an auxotrophic host organism i.e. a selection gene which complements the respective gene deleted at the genome of the host organism. Said gene may be the trp-1 gene to be used with a eukaryotic organism depleted of the phosphoribosylanthranilate isomerase enzyme such as a trp yeast; the URA3 gene to be used with a eukaryotic organism depleted of the orotidine 5-phosphate decarboxylase enzyme such as a ura$^-$ yeast; the tk gene to be used with a eukaryotic organism depleted of the thymidine kinase enzyme; the ada gene to be used with a eukaryotic organism depleted of the adenosine deaminase enzyme; the Apt gene to be used with a eukaryotic organism depleted of the adenine phosphoribosyl-transferase enzyme of the Hprt gene to be used with a eukaryotic organism depleted of the Hypoxanthine-guanine phosphoribosyl-transferase enzyme. It is to be pointed out that the eukaryotic expression vector of the present invention may also contain a selectable marker which can be used in prokaryotes or in eukaryotes such as a bacterial gene having resistance to an antibiotic such as ampicillin, neomycin, hygromycin, geneticin, carboxin, nourseothricin or G418.

By « promoter of eukaryotic type» in the present invention is meant both a promoter, constitutive or inducible, adapted for any eukaryotic cell and a promoter, constitutive or inducible, specific to a particular tissue. A promoter adapted for any eukaryotic cell which can be used in the present invention is notably chosen from among the CMV promoter (CytoMegaloVirus) and in particular intron A of this promoter; the CYC1-TetO-7 promoter (cf. experimental section for more detail); the early SV40 promoter (Simian Virus 40), the HSV promoter (Herpes Simplex Virus) and TEV promoter (Tobacco Etch Virus). One promoter specific to a particular tissue which can be used in the present invention is typically chosen from among the PEPCK promoter (PhosphoEnolPyruvate CarboxyKinase) specific to hepatocytes, the SPA promoter (Surfactant proteinA) specific to epithelial cells in particular pulmonary cells; the MLC1:3 promoter (Myosin light chain) specific to myoblasts, the CEA promoter (CarcinoEmbryonic Antigen) specific to tumour cells and the MCK promoter (Muscle Creatine Kinase) specific to skeletal muscle cells. In addition, a yeast inducible promoter which can be used in the present invention can be the GAL1 promoter inducible by galactose, the AOX1 promoter inducible by methanol, the ADH-2 promoter inducible by glucose depletion, the MET15 promoter inducible by methionine depletion or the CUP1 promoter inducible by copper ions. In the eukaryotic expression vector subject of the present invention, the promoter can be associated with one or more transcriptional regulation sequences i.e. enhancers.

Advantageously, the eukaryotic expression vector of the present invention comprises, operationally linked together, a promoter of eukaryotic type, a nucleotide sequence encoding a fusion protein and a eukaryotic transcription terminating signal comprising a cleavage site and/or polyA signal. By « operationally linked together» in the invention is meant elements linked together so that the functioning of one of the elements is affected by the functioning of the other. For example, a promoter is operationally linked to a coding sequence when it is capable of affecting the expression thereof. The elements regulating the transcription, translation and maturation of the peptides which may be contained in the vector are known to persons skilled in the art who are capable of choosing from among these in relation to the eukaryotic host organism in which expression or cloning are to be performed.

By « fusion protein» is meant a protein comprising at least two polypeptides from one same source or from different sources functionally linked to each other whereby each polypeptide of the fusion protein maintains its own function or activity.

The two polypeptides of the fusion protein can be directly linked to each other via a peptide bond, or indirectly via a spacer arm (or link arm or junction agent) separating the two polypeptides. The $2^{nd}$ polypeptide may be directly or indirectly bound to the C-terminal or N-terminal end of the $1^{st}$ polypeptide. If the bond is a direct bond, the nucleotide sequences encoding each of the polypeptides are linked to one other in 5'-3' direction whereby the translation frame of the encoded polypeptides is not deteriorated.

In the eukaryotic expression vector of the invention, the nucleotide sequence encodes a fusion protein comprising a $1^{st}$ polypeptide corresponding to a DNA binding protein and belonging to the partitioning system of bacterial DNA, a derivative or fragment thereof. The present invention therefore concerns a eukaryotic expression vector comprising a nucleotide sequence encoding a fusion protein comprising a $1^{st}$ polypeptide corresponding to a DNA binding protein belonging to the partitioning system of bacterial DNA, a derivative or fragment thereof. More particularly, the present invention concerns a eukaryotic expression vector comprising a nucleotide sequence encoding a fusion protein comprising a $1^{st}$ polypeptide corresponding to a DNA binding protein, without any other factor being necessary for this binding, and belonging to the partitioning system of bacterial DNA, a derivative or fragment thereof. « Without any other factor being necessary for this binding» means that the binding to DNA is solely dependent on the DNA binding protein belonging to the bacterial DNA partitioning system used and on the recognition site at the DNA, no other factor in particular organic factor and more particularly protein factor being involved in this binding.

By « partitioning system of bacterial DNA» is meant the system involved in the partitioning (or segregation) of the chromosome(s) and optionally of the plasmid(s) during mitosis in bacteria. This system is known in the literature as the « par system» .

As previously explained, the DNA partitioning system in bacteria is a 3-element system comprising (i) a DNA sequence known in the literature under the term ParS or centromeric sequence; (ii) a protein specifically binding to this DNA sequence and known in the literature under the term ParB and (iii) a protein having ATPase activity known in the literature under the term ParA. Therefore by « DNA binding protein and belonging to the partitioning system of bacterial DNA» is meant the ParB protein. It is to be noted however that the DNA binding protein belonging to the partitioning system of bacterial DNA may also be called the « protein binding a sequence of centromeric type» (i.e. a sequence playing the role of centromere) or by any other name such as for *Bacillus subtilis* for which this protein is called SpoOJ.

Any DNA binding protein belonging to the partitioning system of bacterial DNA can potentially be used in the present invention for as long as this binding does not depend on another factor such as the IHF protein or a transcription factor such as Gal4. In this manner, in the fusion protein used in the present invention, the binding to DNA depends solely on the $1^{st}$ polypeptide corresponding to a DNA binding protein belonging to the partitioning system of bacterial DNA, a derivative or fragment thereof. Advantageously, the DNA binding protein belonging to the partitioning system of bacterial DNA is capable, once bound to the DNA, of recruiting other copies of itself and of spreading over the DNA. Persons skilled in the art are capable of verifying, using a routine approach, whether or not a DNA binding protein belonging to the partitioning system of bacterial DNA can be used in the present invention. For this purpose, such persons may use several tests including for example the formation of fluorescent foci or gel shift (EMSA). EMSA is a test in which gel electrophoresis of the DNA sequence recognised by the DNA binding protein belonging to the partitioning system of bacterial DNA is performed in the presence or absence of the recombinant protein. If, in the presence of the protein, the DNA migrates a shorter distance than in the absence of the protein, this protein is capable alone of binding to the DNA and is therefore included in the scope of the present invention. The recruitment of other copies of the DNA binding protein can be visualised by placing a DNA sequence having a recognition site in contact with several DNA binding proteins belonging to the partitioning system of bacterial DNA, tagged and in particular fluorescent. Recruitment is substantiated by a fluorescent focus at the DNA.

The DNA binding proteins belonging to the partitioning system of bacterial DNA, their amino acid sequence and/or the nucleotide sequences encoding the same are accessible in the databases of amino acid or nucleotide sequences such as Genbank or NCBI genome project for those bacteria whose genome has been sequenced in full or in part. If necessary, those skilled in the art may use already described ParB protein sequences to identify the analogue of the latter in a bacterium whose genome has not been fully sequenced or for which the DNA binding protein belonging to the partitioning system of bacterial DNA is not yet known.

Advantageously, the DNA binding protein belonging to the partitioning system of bacterial DNA is a ParB protein derived from *Burkholderia cenocepacia*. More particularly this protein is chosen from among:

the ParB protein encoded by chromosome 1 of Bcc designated « ParB-c1» such as the protein of Bcc strain J2315 accessible in NCBI genome project under No YP-002229191;

the ParB protein encoded by chromosome 2 of Bcc designated « ParB-c2» such as the protein of Bcc strain J2315 accessible in NCBI genome project under No YP-002232636 and corresponding to the protein SEQ ID NO: 2 in the appended sequence listing;

the ParB protein encoded by chromosome 3 of Bcc designated « ParB-c3» such as the protein of Bcc strain J2315 accessible in NCBI genome project under No YP-002153395 and corresponding to the protein SEQ ID NO: 4 in the appended sequence listing; and the ParB protein encoded by the plasmid of Bcc designated « ParB-p1» such as the protein of plasmid pBCJ2315 of Bcc strain J2315 accessible in NCBI genome project under No YP-002235439, a derivative or fragment thereof.

By « derivative of the DNA binding protein belonging to the partitioning system of bacterial DNA» is meant peptides which have at least 30%, at least 40%, at least 45%, at least 50%, at least 55%, at least 60%, at least 65%, at least 70%, at least 75%, at least 80%, at least 85%, at least 90%, at least 95% and/or at least 99% identity respectively with the sequence of a DNA binding protein belonging to the partitioning system of bacterial DNA and in particular with the sequences given above. This definition of derivative therefore covers the homologues of the DNA binding proteins belonging to the partitioning system of bacterial DNA and notably of the ParB proteins of Bcc, and in particular homologues of ParB-c1, ParB c2 ParB-c3 and ParB-p1 of strain J2315. By « homologue of a ParB protein of Bcc» is meant both a different or equivalent form of a ParB protein of Bcc of strain J2315, isolated from a strain or species different from *Burkholderia cenocepacia*.

By « percentage identity» between two amino acid sequences (or between two nucleotide sequences as envisaged below) in the present invention is meant a percentage of identical amino acid (or nucleotide) residues between the two compared sequences, this percentage being obtained after performing the best alignment (optimum alignment) between the two sequences. Those skilled in the art know different techniques with which to obtain such a percentage identity entailing homology algorithms or computer programmes such as BLAST.

Percentage identity is statistical and the differences between the two sequences are distributed along these sequences. The differences between the two sequences may consist of different types of modifications of the sequences: deletions, substitutions or additions of amino acid (or nucleotide) residues.

In addition, when the percentage identity of sequences is used with reference to proteins, it is known that residues which are not identical often differ through substitutions of conserved amino acids in which the amino acids are substituted by other amino acids having similar chemical properties such as charge, hydrophilic or hydrophobic nature, which therefore does not change the functional properties of the molecule. When the sequences differ through conservative substitutions, the percentage identity of sequences can be adjusted upwards to take into account the conservative nature of the substitutions. The sequences which differ through such conservative substitutions are said to have "sequence similarity" or "similarity". The means for obtaining such adjustment are well known to persons skilled in the art. Typically this consists of counting a conservative substitution as a partial mismatch, rather than a total mismatch, thereby increasing the percentage identity of sequences.

Tables of conservative substitutions listing amino acids similar from a functional viewpoint are well known in the state of the art. For example, the 8 following groups each contain amino acids which are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M).

In the present invention, a derivative of a DNA binding protein belonging to the partitioning system of bacterial DNA is a polypeptide having similarity in the sequence of amino acids of at least 40%, of at least 50%, of at least 60%, of at least 70%, of at least 80%, of at least 90% or of at least 95% with the amino acid sequence of a DNA binding protein belonging to the partitioning system of bacterial DNA.

Therefore the modifications between a DNA binding protein belonging to the partitioning system of bacterial DNA and a derivative thereof, and in particular between the ParB proteins of Bcc and their derivatives, can consist of substitutions, additions or deletions of amino acids. Irrespective of the type of modifications applied, these do not destroy the capability of a derivative of a DNA binding protein belonging to the partitioning system of bacterial DNA and in particular of a ParB protein of Bcc to bind specifically to the DNA without any other factor being required for such binding. The envisaged substitutions may be substitutions between equivalent amino acids i.e. amino acids having structural homologies or not substantially modifying the properties of a DNA binding protein belonging to the partitioning system of bacterial DNA. As a variant, the envisaged substitutions may be substitutions by non-equivalent amino acids i.e. amino acids not having structural homology. These modifications do not however destroy the capability of a derivative of a DNA binding protein belonging to the partitioning system of bacterial DNA, and in particular of a ParB protein of Bcc, to bind specifically to the DNA.

The derivatives of DNA binding proteins belonging to the partitioning system of bacterial DNA, and in particular derivatives of ParB proteins of Bcc may also, compared with the sequences of DNA binding proteins belonging to the partitioning system of bacterial DNA and particularly compared with the ParB proteins of Bcc whose sequences were given above, have at least one additional C-terminus and/or N-terminus amino acid, a post-translational modification and/or chemical modification in particular glycosylation, amidation, acylation, acetylation, ethylation, and a protecting group which prevents degradation thereof. Advantageously the derivatives, compared with the sequences of DNA binding proteins belonging to the partitioning system of bacterial DNA and particularly compared with the ParB proteins of Bcc and more particularly compared with the ParB proteins of Bcc whose sequences were given above, may have 1, 2, 3, 4, 5, 6, 7, 8, 9 or 10 additional C-terminus amino acids and/or 1, 2, 3, 4, 5, 6, 7, 8, 9 or 10 additional N-terminus amino acids.

The derivatives of DNA binding proteins belonging to the partitioning system of bacterial DNA and in particular derivatives of the ParB proteins of Bcc may also be those of which one (or more) amino acid(s) is (are) chosen from the group consisting of enantiomers, diastereoisomers, D-conformation natural amino acids, beta amino acids, substituted alpha amino acids, rare amino acids in particular hydroxyproline, hydroxylysine, allo-hydroxylysine, 6-N-methyllysine, N-ethylglycine, N-methylglycine, N-ethylasparagine, allo-isoleucine, N-methylisoleucine, N-methylvaline, pyroglutamine, aminobutyric acid and synthetic amino acids particularly ornithine, norleucine, norvaline, cyclohexylalanine and the omega amino acids. The derivatives of DNA binding proteins belonging to the partitioning system of bacterial DNA and particularly derivatives of the ParB proteins of Bcc according to the invention also cover retropeptides and retro-inverso peptides, and also peptides, the side chain one or more amino acids of which are substituted by groups which do not modify the capability of the derivatives to bind specifically to DNA.

Therefore, irrespective of the type of envisaged derivative, a derivative of a DNA binding protein belonging to the partitioning system of bacterial DNA and in particular a derivative of a ParB protein of Bcc maintains its capability of specifically binding to DNA, said binding not being dependent on any factor in particular any organic factor and more particularly any protein factor.

By a «fragment of a DNA binding protein belonging to the partitioning system of bacterial DNA» in the present invention is meant every part or every portion of a DNA binding protein belonging to the partitioning system of bacterial DNA and in particular of a ParB protein of Bcc which has maintained its capability of specifically binding to DNA, said binding not depending on any other factor in particular any organic and more particularly any protein factor. A fragment of a DNA binding protein belonging to the partitioning system of bacterial DNA and in particular a fragment of a ParB protein of Bcc has at least one amino acid less at the C-terminal end and/or N-terminal end compared with the DNA binding protein belonging to the partitioning system of bacterial DNA, and in particular compared with the ParB protein of Bcc and more particularly compared with the ParB proteins of Bcc whose sequences were described above.

Advantageously the fragment of a DNA binding protein belonging to the partitioning system of bacterial DNA, and in particular of a ParB protein of Bcc, contains at least the motif involved in DNA binding. Said motif corresponds to the motif having a helix-turn-helix structure (HTH) such as described in Dubarry et al, 2006. The HTH motif notably corresponds to the sequence lying between amino acids 202 and 225 of sequence SEQ ID NO: 2 in the appended sequence listing. It is to be noted however that not every DNA binding protein belonging to the partitioning system of bacterial DNA necessarily has a DNA binding motif of HTH structure. The homologue of the ParB protein in the bacterium TP228 for example has a motif of ribbon-helix-helix structure at the C-terminal end (Golovanov et al, 2003).

Evidently the fusion protein comprising a $1^{st}$ polypeptide corresponding to a DNA binding protein belonging to the partitioning system of bacterial DNA, and in particular a ParB protein of Bcc or one of its derivatives or fragments, does not cover a protein of the bacterial partitioning system or one of its homologues as such.

In the eukaryotic expression vector of the present invention, the nucleotide sequence encodes a fusion protein comprising a $2^{nd}$ polypeptide which is either an easily detectable polypeptide or a polypeptide involved in the regulation of gene expression.

By «easily detectable polypeptide» in the present invention is meant a polypeptide which can be detected by applying an appropriate detection technique that is advantageously non-invasive such as microscopy, scintigraphy and fluorescence. A fusion protein comprising such an easily detectable polypeptide particularly allows the identification and locating of DNA sites to which the DNA binding protein belonging to the partitioning system of bacterial DNA in particular a ParB protein of Bcc is able to bind, this protein corresponding to the other polypeptide of the fusion protein.

In a $1^{st}$ embodiment, the easily detectable polypeptide may be an enzyme capable of generating a detectable and optionally quantifiable signal under particular conditions such as when placed in the presence of an adapted substrate. As illustrative but non-limiting examples, mention can be made of alkaline phosphatase, peroxidase, acetylcholine esterase (AChE), glucose amylase and lysozyme.

In a $2^{nd}$ embodiment, the easily detectable polypeptide may be a bioluminescent or fluorescent polypeptide such as aequorin; obeline; luciferase and fluorescent proteins such as Green Fluorescent Protein (GFP), e-GFP protein (enhanced GFP), enhanced Cyan Fluorescent Protein (eCFP), enhanced Yellow Fluorescent Protein (eYFP), enhanced Blue Fluorescent Protein (eBFP), the red fluorescent proteins DsRed and Keima and their variants such as Photoactivatable GFP protein at 405 nm (PA-GFP), pH-sensitive GFP protein (PHluorin), Cerulean protein, azurite protein, Venus protein, mCherry protein and Citrin protein.

By «polypeptide involved in the regulation of gene expression» in the present invention is meant a polypeptide which, when present, increases or reduces the expression of at least one gene, compared with the expression of this same gene under the same operating conditions but in the absence of this polypeptide.

Persons skilled in the art know different types of polypeptides which may influence the expression of one (or more) gene(s). Advantageously such a polypeptide can be chosen from among a positive or negative transcription factor, a general transcription factor, a regulator of the expression of a promoter, a chromatin remodelling factor and a factor modifying the location of an adjacent gene, a derivative or a fragment thereof.

For example, a polypeptide involved in the regulation of gene expression may act positively or negatively, directly or indirectly, either on the recruitment of the transcriptional complex or on the state of the chromatin, or on the location of the gene the expression of which is to be regulated. A polypeptide acting on the state of chromatin may act on DNA decompaction, on DNA unfurling, on the methylation of cytosines or on the acetylation of histones. One polypeptide acting on the location of the gene the expression of which is to be regulated may be a factor allowing the addressing or recruiting of the adjacent gene at a particular organelle or particular cell zone. As non-limiting examples, the particular organelle or particular zone may be a cell membrane or nuclear periphery. This addressing may involve a protein specific to a particular organelle or to a particular cell zone or a monoclonal or polyclonal antibody directed against said protein, a derivative or fragment thereof.

By «derivative» of a factor or regulator such as defined above is meant a polypeptide having at least 40% similarity and/or at least 30% identity with a factor or regulator such as defined above that is known and capable of influencing gene expression, negatively or positively. By «fragment» of a factor or regulator such as defined above is meant any part or any portion of a factor or regulator such as defined above which has maintained its capability to influence gene expression. In addition, the preferred embodiments described for the derivatives and fragments of a DNA binding protein belonging to the partitioning system of bacterial DNA apply mutatis mutandis to the derivatives and fragments of the factors or regulators such as defined above.

More particularly, a polypeptide involved in the regulation of gene expression is chosen from the list of non-exhaustive examples given below:
  the transcription factors TFIIA, TFIIB, TFIID, TRIIE, TFIIF, TFIIH, NF-KappaB, SP1, a heat shock factor;
  a lamin, a membrane protein, an antibody or a an antibody fragment directed against a membrane protein;
  a nuclear receptor such as an oestrogen receptor, a retinoic acid receptor, a glucocorticoid receptor, an androgen receptor, a receptor of 3-ketosteroids or a receptor of thyroid hormones;
  an acetylase, deacetylase, methyl-transferase, poly ADP-ribosyltransferase, ubiquitin ligase, phosphatase, kinase or sumoylase.

In the eukaryotic expression vector of the present invention, the nucleotide sequence encodes a fusion protein comprising a $1^{st}$ polypeptide and a $2^{nd}$ polypeptide such as previously defined, said nucleotide sequence further able to encode an intracellular localization signal.

However, since the fusion proteins used in the present invention may be of small size, in particular thanks to the size of the 1$^{st}$ polypeptide contained therein, the presence of an intracellular localization signal is not compulsory, the fusion proteins able freely to diffuse within the cellular and nuclear volume.

When the fusion protein comprises an intracellular localization signal operationally linked to the 1$^{st}$ and 2$^{nd}$ polypeptides such as previously defined, this signal may be a nuclear localization signal. A said signal attached to the end of one of the two polypeptides of the fusion protein, without affecting the function of one or other of these polypeptides, promotes the transport of the fusion protein within the cellular nucleus. Persons skilled in the art have knowledge of different intracellular localization signals and in particular of different nuclear localization signals which can be used in the present invention.

The present invention also concerns certain fusion proteins encoded by the nucleotide sequence of the eukaryotic expression vector such as previously defined.

Therefore in a 1$^{st}$ embodiment, the fusion protein of the invention comprises:
  a 1$^{st}$ polypeptide corresponding to a DNA binding protein belonging to the partitioning system of bacterial DNA, without any other factor being required for such binding, a derivative or fragment thereof in particular such as previously defined; and
  a 2$^{nd}$ polypeptide involved in the regulation of gene expression, in particular such as previously defined.

In a 2$^{nd}$ embodiment, the fusion protein of the invention comprises:
  a 1$^{st}$ polypeptide corresponding to a ParB protein derived from *Burkholderia cenocepacia*, a derivative or fragment thereof in particular such as previously defined; and
  a 2$^{nd}$ polypeptide that is easily detectable in particular such as previously defined.

Irrespective of the embodiment, the fusion protein of the present invention may optionally comprise an intracellular localization signal, in particular such as previously defined.

The present invention also concerns a polynucleotide coding for a fusion protein such as previously defined.

Therefore the present invention also concerns an isolated polynucleotide chosen from among the different polynucleotides below:
  i) a polynucleotide encoding a fusion protein of the invention such as previously defined;
  ii) a polynucleotide complementary to the polynucleotide such as defined under item (i);
  iii) a polynucleotide of at least 14 nucleotides and in particular at least 18 nucleotides, capable of hybridizing under conditions of high stringency with the polynucleotides such as defined under items (i) and (ii).

By a « polynucleotide » H in the present invention is meant a nucleic acid, nucleic sequence, nucleic acid sequence, an oligonucleotide, a polynucleotide sequence, a nucleotide sequence, single-strand DNA, double-strand DNA or RNA. A polynucleotide of the present invention comprises natural nucleotides and optionally non-natural nucleotides.

The polynucleotide of the invention does not correspond to a nucleotide sequence in its natural state i.e. in its natural chromosomal environment. The polynucleotide does not correspond either to a natural polynucleotide coding for a polypeptide such as the 1$^{st}$ and 2$^{nd}$ polypeptides of the present invention. On the contrary, the polynucleotide of the invention was isolated and optionally purified and its environment was consequently modified. The polynucleotide of the invention may also be obtained by genetic recombination or chemical synthesis.

The high stringency conditions correspond to conditions of temperature and ionic strength which allow maintained hybridization between two complementary nucleotide sequences. Those skilled in the art will know how to determine the conditions of high stringency that are best adapted, in particular in relation to the size of the nucleotide sequences and with reference to the teaching by Sambrook et al. (Molecular cloning, 1989, Noland C. ed., New York: Cold Spring Harbor Laboratory Press). As a non-limiting, illustrative example, the conditions of high stringency at the hybridization step for the purpose of defining the polynucleotides of item (iii) described above, are advantageously the following: hybridization, in particular of DNA-DNA or DNA-RNA type, performed in two steps: (1) pre-hybridization at 42° C. for 3 h in a phosphate buffer (20 mM, pH 7.5) comprising a solution containing 0.75 M NaCl, 0.075 M sodium citrate, 50% formamide, 7% de sodium dodecyl sulfate (SDS), 10×Denhardt's, 5% de dextran sulfate and 1% salmon sperm DNA; (2) hybridization properly so-called for 20 h at a temperature dependent upon the size of the probe (e.g. 42° C. for a probe of size >100 nt) followed by 2 20-min washings at 20° C. in a solution containing 0.3 M NaCl, 0.03 M sodium citrate and 2% SDS; 1 20-min washing at 20° C. in a solution containing 0.015 M NaCl, 1.5 mM sodium citrate and 0.1% SDS. The last washing is conducted in a solution containing 0.015 M NaCl, 1.5 mM sodium citrate and 0.1% SDS for 30 min at 60° C. for a probe of size >100 nt.

The polynucleotide of item (iii) i.e. capable of hybridizing under high stringency conditions with the polynucleotides such as defined under items (i) and (ii), comprises at least 20, at least 50, at least 100, at least 150, at least 200, at least 250 or at least 300 nucleotides.

The polynucleotide of the present invention comprises at least one nucleotide sequence having at least 30%, at least 40%, at least 45%, at least 50%, at least 55%, at least 60%, at least 65%, at least 70%, at least 75%, at least 80%, at least 85%, at least 90%, at least 95% and/or at least 99% identity with one of the nucleotide sequences coding for a DNA binding protein belonging to the partitioning system of bacterial DNA such as previously defined, in particular a DNA binding protein belonging to the partitioning system of bacterial DNA is a ParB protein derived from *Burkholderia cenocepacia* and more particularly the ParB protein carried by chromosome 1 of Bcc designated « ParB-c1 », the ParB protein carried by chromosome 2 of Bcc designated « ParB-c2 », the ParB protein carried by chromosome 3 of Bcc designated « ParB-c3 » and the ParB protein carried by the plasmid of Bcc designated « ParB-p1 ».

For example, the polynucleotide of the present invention comprises at least one nucleotide sequence having at least 30%, at least 40%, at least 45%, at least 50%, at least 55%, at least 60%, at least 65%, at least 70%, at least 75%, at least 80%, at least 85%, at least 90%, at least 95% and/or at least 99% identity with sequence SEQ ID NO: 1 in the appended sequence listing (i.e. the sequence encoding protein ParB carried by chromosome 2 of Bcc designated « ParB-c2 ») or with sequence SEQ ID NO: 3 in the appended sequence listing (i.e. the sequence encoding protein ParB carried by chromosome 3 of Bcc designated « ParB-c2 »).

The polynucleotide of the invention evidently also covers the sequences encoding fragments of the previously envisaged DNA binding proteins belonging to the partitioning system of bacterial DNA, the sequences having at least 30%, at least 40%, at least 45%, at least 50%, at least 55%, at least 60%, at least 65%, at least 70%, at least 75%, at least 80%, at least 85%, at least 90%, at least 95% and/or at least 99% identity with the sequences coding for these fragments and the sequences complementary to said sequences. From the sequences of the envisaged fragments and the nucleotide sequence encoding the DNA binding proteins belonging to the partitioning system of bacterial DNA, it is easy for those skilled in the art to identify the nucleotide sequence coding for a particular fragment.

The polynucleotide of the invention evidently also covers the sequences encoding the previously envisaged derivatives of the DNA binding proteins belonging to the partitioning system of bacterial DNA, the sequences having at least 30%, at least 40%, at least 45%, at least 50%, at least 55%, at least 60%, at least 65%, at least 70%, at least 75%, at least 80%, at least 85%, at least 90%, at least 95% and/or at least 99% identity with the sequences coding for these derivatives and the sequences complementary to said sequences. From the sequences of the envisaged derivatives and the nucleotide sequence coding for the DNA binding proteins belonging to the partitioning system of bacterial DNA, it is easy for those skilled in the art to identify the nucleotide sequence coding for a particular derivative.

In addition, the polynucleotide of the invention comprises at least one other nucleotide sequence encoding either an easily detectable polypeptide or a polypeptide involved in the regulation of gene expression, such as previously envisaged, the sequences having at least 30%, at least 40%, at least 45%, at least 50%, at least 55%, at least 60%, at least 65%, at least 70%, at least 75%, at least 80%, at least 85%, at least 90%, at least 95% and/or at least 99% identity with the sequences coding for these polypeptides and the sequences complementary to said sequences.

When (ribo)nucleic acids are compared, their similarity can also be determined. In this case, similarity is assessed at codon level. Two codons are similar if they are two different codons coding for the same amino acid or two different codons coding for two similar amino acids.

The polynucleotide of the present invention comprises at least one nucleotide sequence having at least 40%, at least 45%, at least 50%, at least 55%, at least 60%, at least 65%, at least 70%, at least 75%, at least 80%, at least 85%, at least 90%, at least 95% and/or at least 99% similarity with one of the nucleotide sequences coding for a DNA binding protein belonging to the partitioning system of bacterial DNA such as previously defined, in particular a DNA binding protein belonging to the partitioning system of bacterial DNA is a ParB protein derived from Burkholderia cenocepacia and more particularly the ParB protein carried by chromosome 1 of Bcc designated « ParB-c1» the ParB protein carried by chromosome 2 of Bcc designated « ParB-c2», the ParB protein carried by chromosome 3 of Bcc designated « ParB-c3» and the ParB protein carried by the plasmid of Bcc designated « ParB-p1».

Therefore, the polynucleotide of the present invention comprises at least one nucleotide sequence having a least 40%, at least 45%, at least 50%, at least 55%, at least 60%, at least 65%, at least 70%, at least 75%, at least 80%, at least 85%, at least 90%, at least 95% and/or at least 99% similarity with sequence SEQ ID NO: 1 in the appended sequence listing (i.e. the sequence coding for the ParB protein carried by chromosome 2 of Bcc designated « ParB-c2») or with sequence SEQ ID NO: 3 in the appended sequence listing (i.e. the sequence coding for the ParB protein carried by chromosome 3 of Bcc designated « ParB-c2»).

The polynucleotide of the invention evidently also covers the sequences encoding the previously envisaged fragments of the DNA binding proteins belonging to the partitioning system of bacterial DNA, the sequences having at least 40%, at least 45%, at least 50%, at least 55%, at least 60%, at least 65%, at least 70%, at least 75%, at least 80%, at least 85%, at least 90%, at least 95% and/or at least 99% similarity with the sequences encoding these fragments and the sequences complementary to said sequences. From the sequences of envisaged fragments and the nucleotide sequence encoding the DNA binding proteins belonging to the partitioning system of bacterial DNA, it is easy for those skilled in the art to identify the nucleotide sequence coding for a particular fragment.

The polynucleotide of the invention also evidently covers the sequences coding for the previously envisaged derivatives of the DNA binding proteins belonging to the partitioning system of bacterial DNA, the sequences having at least 40%, at least 45%, at least 50%, at least 55%, at least 60%, at least 65%, at least 70%, at least 75%, at least 80%, at least 85%, at least 90%, at least 95% and/or at least 99% similarity with the sequences coding for these derivatives and the sequences complementary to said sequences. From the sequences of the envisaged derivatives and from the nucleotide sequence encoding the DNA binding proteins belonging to the partitioning system of bacterial DNA, it is easy for those skilled in the art to identify the nucleotide sequence coding for a particular derivative.

In addition, the polynucleotide of the invention comprises at least one other nucleotide sequence encoding either an easily detectable polypeptide or a polypeptide involved in the regulation of gene expression such as previously envisaged, the sequences having at least 30%, at least 40%, at least 45%, at least 50%, at least 55%, at least 60%, at least 65%, at least 70%, at least 75%, at least 80%, at least 85%, at least 90%, at least 95% and/or at least 99% identity with the sequences encoding these polypeptides and the sequences complementary to said sequences.

Finally, the polynucleotide of the invention may comprise at least one other nucleotide sequence coding for an intracellular localization sequence, in particular such as previously defined.

The present invention also concerns an eukaryotic vector comprising a nucleotide sequence having at least one recognition site recognised by a DNA binding protein belonging to the partitioning system of bacterial DNA. The eukaryotic vector further comprises a selectable marker of eukaryotic type such as previously defined, having at least one recognition site recognised by a DNA binding protein belonging to the partitioning system of bacterial DNA. The eukaryotic vector of the invention is typically in the form of a plasmid.

Advantageously, the eukaryotic vector is an integrative eukaryotic vector. By « integrative eukaryotic vector» is meant a vector of which all or part of the nucleotide sequence is able to be integrated into the genome of the organism in which said vector is inserted. In addition, the integration into the genome of the host organism can take place at a particular predetermined genomic site or randomly. Targeted integration uses homologous recombination. In this case, the integrative eukaryotic vector or a fragment carrying said sequence produced by PCR, has suitable sequences either side of the nucleotide sequence having at least one recognition site recognised by a DNA binding protein belonging to the partitioning system of bacterial DNA, to allow this homologous recombination.

Any recognition site to which a protein binds which belongs to the partitioning system of plasmid or chromosomal DNA of a prokaryote can be used in the present invention. The article by Dubarry et al, 2006 describes different recognition sites recognised by different DNA binding proteins belonging to the partitioning system of bacterial DNA. All these recognition sites come within the scope of the present invention. The recognition site used in the present invention is preferably double-strand.

Advantageously, the recognition site recognised by a DNA binding protein belonging to the partitioning system of bacterial DNA and used in the present invention is of nucleotide sequence (I) or of a sequence complementary to nucleotide sequence (I):

$N_1N_2TN_3N_4N_5N_6CGN_7N_8N_9N_{10}AN_{11}N_{12}$ (I) (SEQ ID NO: 5 in the appended sequence listing) in which the nucleotides $N_1$ and $N_{12}$, the same or different, or chosen from among A, G, C or T and the pairs of nucleotides $(N_6,N_7)$, $(N_5,N_8)$, $(N_4,N_9)$, $(N_3,N_{10})$ and $(N_2,N_{11})$ independently of each other are chosen from the group formed by (A,T), (T,A), (C,G) and (G,C), the nucleotides $N_1$ and $N_{12}$ possibly being optionally absent.

Advantageously, in sequence (I) above, $N_1$ is absent or represents G, C or T; the pair $(N_6,N_7)$ represents (A,T), (T,A) or (G,C); the pair $(N_5,N_8)$ represents (C,G) ou (T,A); the pair $(N_4,N_9)$ represents (A,T), (T,A), (C,G) or (G,C); the pair $(N_3,N_{10})$ represents (G,C) or (T,A); the pair $(N_2,N_{11})$ represents (T,A) or (G,C) and $N_{12}$ is absent or represents A or C.

At the recognition site the symmetric nature ($N_2$ to $N_6$ with $N_7$ to $N_{11}$) is most important for recognition. It is therefore possible that a sequence of same symmetric organization, without necessarily having nucleotide identity, is able to have the same characteristics.

In particular, the recognition site recognised by a DNA binding protein belonging to the partitioning system of bacterial DNA used in the present invention is of nucleotide sequence (II) or a sequence complementary to nucleotide sequence (II):

$N_{13}TTN_{14}N_{15}N_{16}N_{17}CGN_{18}N_{19}N_{20}N_{21}AAC$ (II) (SEQ ID NO: 6 in the appended sequence listing) in which:

$N_{13}$ represents G, C or T;
the pair $(N_{14},N_{21})$ represents (T,A) or (G,C);
the pair $(N_{15},N_{20})$ represents (A,T) or (T,A);
the pair $(N_{16},N_{19})$ represents (T,A) or (C,G);
the pair $(N_{17},N_{18})$ represents (G,C) or (A,T).

Advantageously the recognition site recognised by a DNA binding protein and belonging to the partitioning system of bacterial DNA has a nucleotide sequence chosen from among the following nucleotide sequences:

GTTTATGCGCATAAAC (Sc2; SEQ ID NO: 7 in the appended sequence listing);
CTTTATGCGCATAAAC (Sc2; SEQ ID NO: 8 in the appended sequence listing);
GTTGTCACGTGACAAC (Sc3; SEQ ID NO: 9 in the appended sequence listing);
TTTGTCACGTGACAAC (Sc3; SEQ ID NO: 10 in the appended sequence listing);
CTTGTCACGTGACAAC (Sc3; SEQ ID NO: 11 in the appended sequence listing);
and a sequence complementary to any one of these sequences.

The nucleotide sequence of the optionally integrative eukaryotic vector of the present invention comprises at least 2, at least 3 or at least 4 recognition sites recognised by a DNA binding protein belonging to the partitioning system of bacterial DNA such as previously defined. If the polynucleotide of the present invention comprises at least 2 recognition sites, two consecutive recognition sites may be identical or different from each other. If the polynucleotide of the present invention comprises at least 2 recognition sites, two consecutive recognition sites can be separated by at least 1 nucleotide, in particular at least 10 nucleotides, more particularly at least 50 nucleotides and further particularly at least 100 nucleotides.

The nucleotide sequence of the optionally integrative eukaryotic vector according to the present invention may be natural, synthetic or be obtained by mutation of a natural sequence.

The nucleotide sequence of the optionally integrative eukaryotic vector according to the present invention advantageously comprises a centromeric sequence involved in the bacterial partitioning system. In particular, this centromeric sequence may be a sequence derived from any bacterium such as *Bacillus subtilis, Caulobacter crescentus* etc. . . . . .

In one particular embodiment, the nucleotide sequence of the optionally integrative eukaryotic vector according to the present invention advantageously comprises a centromeric sequence involved in the partitioning system of the bacterium *Burkholderia cenocepacia* (Bcc), a sequence known under the name ParS. Further particularly this nucleotide sequence corresponds to a sequence chosen from among:

the ParS sequence carried by chromosome 1 of Bcc designated « ParS-c1 » which can be obtained from the nucleotide sequence of chromosome 1 of the Bcc strain J2315 accessible in Genbank under No AM 747720, the two recognition sites contained in this sequence respectively lying at nucleotides 26477-26492 and 28403-28418;

the ParS sequence carried by chromosome 2 of Bcc designated « parS-c2 » which can be obtained from the nucleotide sequence of chromosome 2 of Bcc strain J2315 accessible in Genbank under No AM 747721 and corresponding to protein SEQ ID NO: 12 in the appended sequence listing;

the ParS sequence carried by chromosome 3 of Bcc designated « ParS-c3 » which can be obtained from the nucleotide sequence of chromosome 3 of Bcc strain J2315 accessible in Genbank under No AM 747722 and corresponding to protein SEQ ID NO: 13 in the appended sequence listing; » the ParS sequence carried by the plasmid of Bcc designated « ParS-p1 » which can be obtained from the nucleotide sequence of plasmid pBCJ2315 of Bcc strain J2315 accessible in Genbank under No AM 747723, the three recognition sites contained in this sequence respectively lying at nucleotides 92285-92300, 92385-92400 and 92438-92453;

or a sequence complementary to any one of these sequences.

The invention also concerns a eukaryotic host organism transformed by or comprising a eukaryotic expression vector such as previously defined or an optionally integrative eukaryotic vector such as previously defined.

By a « eukaryotic host organisms » is meant any eukaryotic organism, uni- or multicellular, lower or higher, in which a eukaryotic expression vector such as previously defined or an integrative eukaryotic vector such as previously defined is inserted.

Therefore a eukaryotic host organism according to the present invention may be a microorganism such as a yeast or fungus.

As a variant, a eukaryotic host organism according to the present invention may be an animal cell such as an insect cell or mammalian cell and in particular a human cell, hamster cell, monkey cell, rabbit cell, mouse cell, rat cell, etc. . . . ; a plant cell; a plant, or an animal with the exception of a human. In fact the host organism may be a transgenic plant or transgenic animal with the exception of a human.

The host organism of the invention of cell type can be supplied in the form of a culture in suspension, a culture on culture dishes, a tissue culture or organ culture.

Persons skilled in the art know different transformation or transfection methods for the efficient insertion of a eukaryotic expression vector such as previously defined or an integrative eukaryotic vector such as previously defined in a host organism. The insertion of the expression vector according to the invention leads to the production of a fusion protein such as previously defined.

As an example and in non-exhaustive manner this method may be electroporation; lipofection; micro-injection; particle (or biolistic) bombarding; biological transformation of a plant using *Agrobacterium tumefasciens*; transformation via chemical permeabilisation through an increase in temperature, heat shock, treatment with detergents or treatment with polyethyleneglycol; transformation using the DEAE-dextran method or insertion via a virus, a virion or viral particle.

Advantageously, the host organism of the present invention is a host organism transformed by or comprising a eukaryotic expression vector such as previously defined and an optionally integrative eukaryotic vector such as previously defined.

In particular, the host organism of the present invention is a host organism having integrated, in its genome or in the exogenous DNA it contains as plasmid or transposon, the nucleotide sequence having at least one recognition site recognised by a DNA binding protein belonging to the partitioning system of bacterial DNA such as previously defined (i.e. the nucleotide sequence present on the integrative eukaryotic vector of the invention) and expressing the fusion protein such as previously defined (i.e. the fusion protein encoded by the nucleotide sequence present on the eukaryotic expression vector of the invention).

More particularly, the host organism of the present invention transiently expresses the fusion protein such as previously defined. As a variant, the host organism of the present invention constitutively expresses the fusion protein such as previously defined.

As previously explained, the nucleotide sequence having at least one recognition site recognised by a DNA binding protein belonging to the partitioning system of bacterial DNA such as previously defined, can be inserted in the host organism at a particular predetermined site using homologous recombination. Advantageously, in this case, the host organism is a yeast. In this case also, the gene adjacent the insertion site of the nucleotide sequence having at least one recognition site recognised by a DNA binding protein belonging to the partitioning system of bacterial DNA, is known.

As a variant, the insertion in the genome of the host organism can be performed randomly. In this case skilled persons are able, using conventional molecular biology techniques, to determine the position of this insertion. With knowledge of this position, those skilled in the art can select a host organism in which insertion took place at a site of interest. The host organism thus selected can generate a stable cell line such as a stable mammalian cell line.

Whether insertion is made in directed or random manner, it is therefore possible to obtain a host organism in which insertion took place at one or more sites of interest such as a site close to an oncogene, close to a tumour suppressor, close to a gene involved in a genetic disease, etc. . . . .

If, in this case, the fusion protein expressed by the host organism comprises a polypeptide involved in the regulation of gene expression, in particular such as previously defined, it is possible positively or negatively to control the expression of the gene adjacent to the insertion site of the nucleotide sequence having at least one recognition site recognised by a DNA binding protein belonging to the partitioning system of bacterial DNA.

Similarly, it is possible to detect a molecule able to control this expression. By « molecule able to control this expression» is meant a natural or synthetic molecule, in particular a biological or biologically active molecule which can be capable of influencing the expression of a gene. Advantageously this molecule is chosen from among the epitopes; antigens; peptides; oligopeptides; proteins such as an enzyme; antibodies and fragments of antibodies; cellular or membrane receptors; polysaccharides; and nucleic molecules such as single or double-strand DNA, RNA, iRNA, miRNA, an aptamer, PNA (peptide nucleic acid) or LNA (locked nucleic acid). Said molecule may have applications in the field of therapeutics.

The present invention proposes a method for detecting a molecule able to control, positively or negatively, the expression of a gene of interest. This method comprises:
contacting said molecule with a host organism of the present invention in which a fusion protein comprising a polypeptide involved in the regulation of gene expression according to the invention is expressed and in which the nucleotide sequence having at least one recognition site recognised by a DNA binding protein belonging to the partitioning system of bacterial DNA has been inserted close to the gene of interest;
detecting the expression of this gene of interest and comparison with the expression obtained in the absence of said molecule.

If expression is identical whether or not the tested molecule is present, this molecule has no effect on such expression. On the contrary, if a difference exists between the two expressions, the tested molecule has a direct or indirect, positive or negative influence on this expression.

As a variant, if the fusion protein expressed by the host organism comprises an easily detectable polypeptide, it is possible in vivo, to detect the position of a site of interest of genomic DNA or exogenous DNA contained in the host organism, such as a plasmid or transposon, and the dynamics thereof under normal conditions or in the presence of a molecule able to affect this position.

By « molecule able to affect this position» is meant a natural or synthetic molecule, in particular a biological or biologically active molecule, which may be able to modify the position of a gene. Advantageously, this molecule is chosen from among epitopes; antigens; peptides; oligopeptides; proteins such as an enzyme; antibodies and fragments of antibodies; cellular or membrane receptors; polysaccharides; and nucleic molecules such as single or double-strand DNA, RNA, iRNA, an aptamer, PNA or LNA.

The present invention proposes a method for detecting a molecule able to affect the position of a gene or site of interest. This method comprises:
contacting said molecule with a host organism of the present invention in which a fusion protein comprising an easily detectable polypeptide of the invention is expressed, and in which the nucleotide sequence having at least one recognition site recognised by a DNA binding protein belonging to the partitioning system of bacterial DNA has been inserted close to the gene or to the site of interest;

detecting the easily detectable polypeptide and hence the position of the recognition site recognised by a DNA binding protein belonging to the partitioning system of bacterial DNA, and hence also the position of the gene or site of interest, and comparing with the position of the gene or site of interest obtained in the absence of said molecule.

If the position is identical whether or not the tested molecule is present, this molecule has no effect on this expression. On the contrary, if a difference does exist between the two positions, the tested molecule directly or indirectly has an influence on this position.

In one particular embodiment, the site of interest corresponds to a DNA double-strand break. In this case, the tracking of the position of this site of interest allows the study of DNA excision during the repair of this double-strand break (disappearance of the detectable signal emitted by the easily detectable polypeptide) and detection of the molecules involved in this degradation or having an influence on this process. As a further variant, the method of the invention allows the monitoring of at least one of the two ends of the double-strand break and thereby the detection of a molecule involved in the maintaining of the DNA ends flanking the cut site. The molecules identified in this particular embodiment may be of therapeutic interest, notably in the field of cancer research and response to anticancer, genotoxic treatments etc.

As a variant the present invention concerns a method for studying the dynamics of a site or gene of interest in genomic or exogenous DNA contained in the host organism. This method comprises:

providing a host organism according to the present invention in which a fusion protein comprising an easily detectable polypeptide of the invention is expressed, and in which the nucleotide sequence having at least one recognition site recognised by a DNA binding protein belonging to the partitioning system of bacterial DNA has been inserted close to the gene or to the site of interest;

detecting, at least at two different times designated $T_1$ and $T_2$, with $T_2 > T_1$, the easily detectable polypeptide and hence the position of the recognition site recognised by the DNA binding protein belonging to the partitioning system of bacterial DNA, and hence also the position of the gene or of the site of interest, and comparing the position of the gene or site of interest obtained at time $T_1$ with that obtained at time $T_2$.

In this particular form of embodiment, detection can be performed continuously or at different points in time designated $T_n$ with n representing an integer between 1 and 10000, each time $T_x$ being separated from time $T_{x+1}$ with x representing an integer between 1 and 9999, for a time of between 1 ms and 10 h, this separation time possibly being constant or variable.

Therefore the present invention concerns an element of the invention chosen from among an eukaryotic expression vector such as previously defined, a fusion protein such as previously defined, a polynucleotide such as previously defined, a nucleotide sequence such as previously defined, an optionally integrative eukaryotic vector such as previously defined and a host organism such as previously defined for use in controlling the expression of a gene in vivo in a eukaryote or to detect the position, dynamics or degradation (or metabolism) of DNA loci or the recombination or exchange of DNA sequences in vivo in a eukaryote.

The present invention also concerns the use of at least one element of the invention chosen from among a eukaryotic expression vector such as previously defined, a fusion protein such as previously defined, a polynucleotide such as previously defined, a nucleotide sequence such as previously defined, an optionally integrative eukaryotic vector such as previously defined and a host organism such as previously defined, to detect a molecule able to control the expression of a gene in vivo in a eukaryote or able to affect the position, the dynamics or the degradation (or metabolism) of DNA loci or the recombination of exchange of DNA sequences in vivo in a eukaryote.

In these uses of the system subject of the present invention, the DNA loci and sequences can either be endogenous, or exogenous and in particular on a plasmid or transposon.

Other characteristics and advantages of the present invention will become further apparent to those skilled in the art on reading the examples below given as non-limiting illustrations with reference to the appended drawings.

BRIEF DESCRIPTION OF THE DRAWINGS

FIG. 9 gives examples of movement of the HML locus over time using the ParS-c2/ParB-c2-mCherry localization system.

FIG. 10 illustrates the monitoring of the position of the fluorescent label at HML as a function of time. FIG. 10A shows the pathway of HML during acquisition. FIG. 10B shows the characterisation of HML movement using Mean-Square displacement (MSD) analysis.

DETAILED DESCRIPTION OF PARTICULAR EMBODIMENTS

I. Techniques used.

I.1. Construction of ParB Expression Vectors.

Figure 1A:
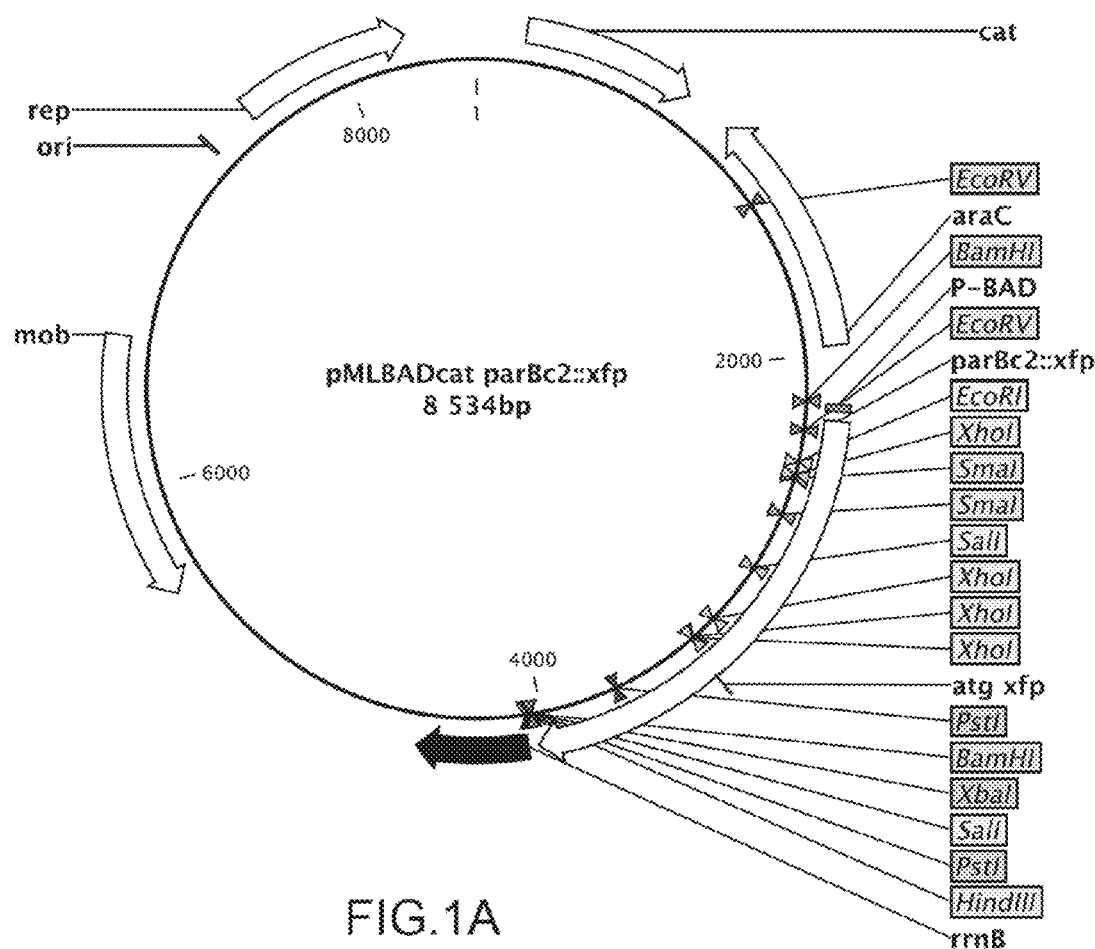
FIG. 1 gives the circular diagram of the pMLBADcat-ParB-c2:: mCherry plasmid (FIG. 1A), of the pMLBADcat-ParB-c2::eGFP plasmid (FIG. 1B), of pDAG512 plasmid (FIG. 1C) and of the pDAG514 plasmid (FIG. 1D).
Figure 1B:
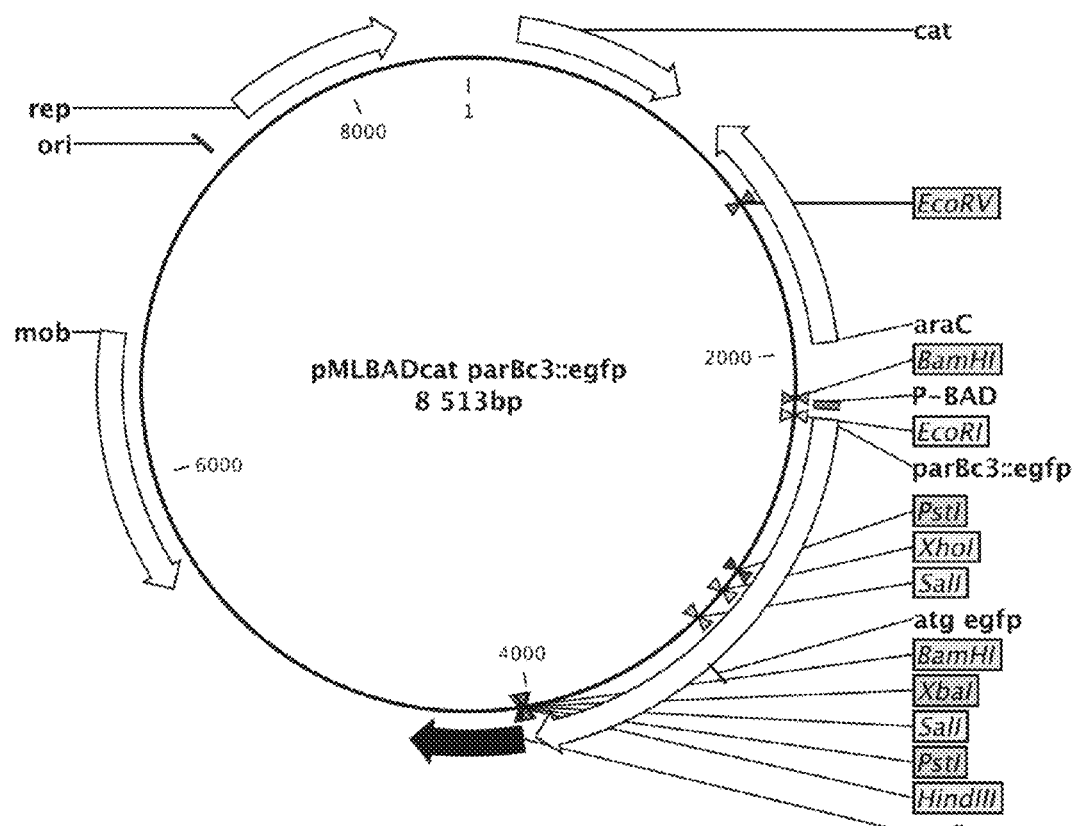

ParB-c2-mCherry and ParB-c3-GFP were amplified using PCR from the plasmids pMLBADcat-ParB-c2:: mCherry (FIG. 1A) and pMLBADcat-ParB-c2:: eGFP (FIG. 1B) respectively with the following primers E and F:

E: 5'-ATTAGCGGATCCTACCTGACGCTTTTTA-3' (SEQ ID No: 14 in the appended sequence listing); and F: 5'-GGAATTGCGGCCGCTTACTTGTACA-GCTCGTCCA-3' (SEQ ID NO: 15 in the appended sequence listing).

The PCR products were BamH1/Not1 digested then inserted in the expression vectors of pCM189 yeast for ParB-c2-mCherry and pCM184 for ParB-c3-GFP digested with BamH1/Not1 to create pFG7 and pFG8.

For the mammalian cells, the peGFP-c2 plasmid by Clontech© (GenBank Accession #: U57606) was digested with Nhe1/HindIII to remove the GFP encoding sequence. A Nhe1/HindIII fragment containing either ParB-c2-mCherry or ParB-c3-GFP of the plasmids pMLBADcat-ParB-c2:: mCherry or pMLBADcat-ParB-c2:: eGFP was then inserted in the plasmids digested with peGFP-c2 to create pFG9 and pFG10.

I.2. Construction of the Plasmids Containing the ParS Sequences.

Figure 1C:
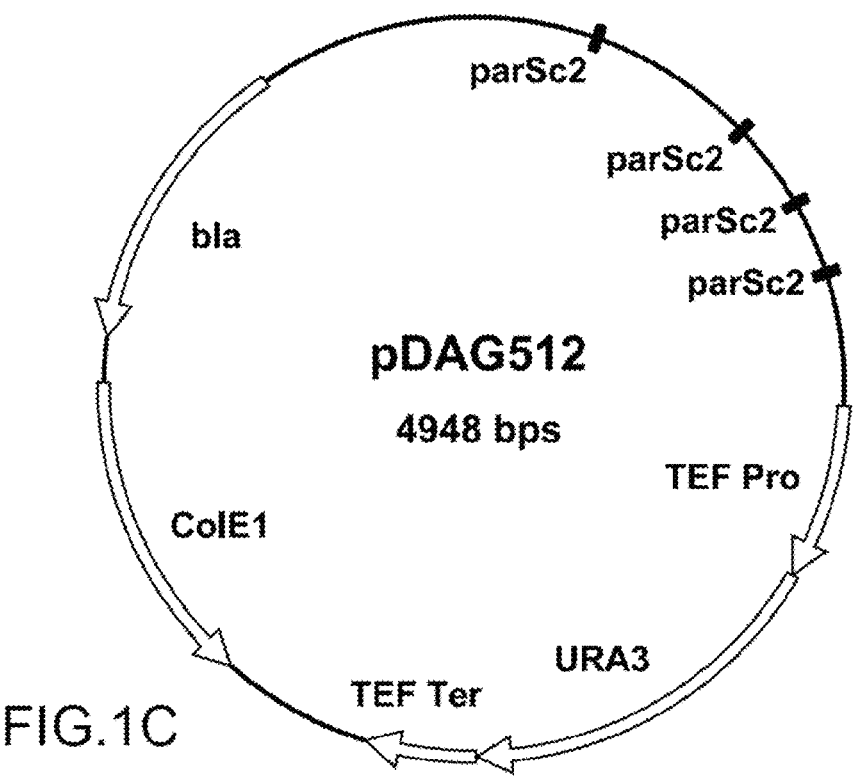
Figure 1D:
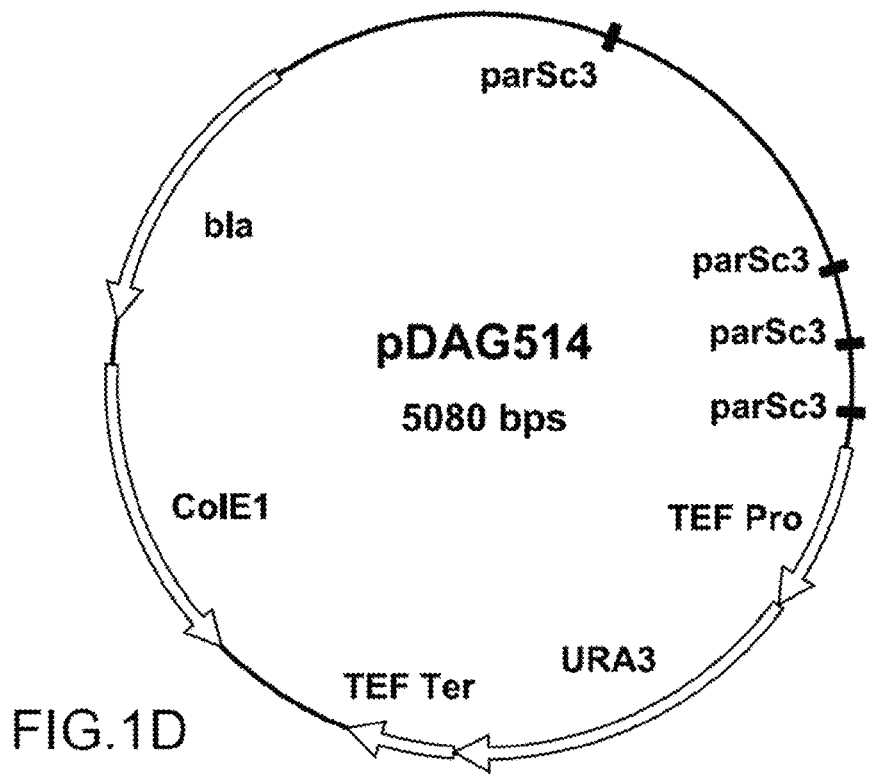

The plasmids containing the bacterial sequences ParS-c2 and ParS-c3 were previously cloned (Dubarry et al, 2006). The yeast shuttle plasmids pDAG512 (ParS-c2; FIG. 1C) and pDAG514 (ParS-c3; FIG. 1D) were digested with BglII/Spe1 to excise the URA3 marker.

The linear vectors were then associated with a BglII/Spe1 fragment containing either the NAT marker or the Hygro marker of plasmids pAG25 and pAG32 respectively, to create the plasmids pFG2 and pFG4.

For the vectors of mammalian cells, a BamH1/BglII fragment containing ParS-c2 or ParS-c3 was ligated in a pMSCV-Hygro vector (Clontech©, Cat. No. 634401) digested with BamH1 to create pFG5 and pFG6.

I.3. Amplification of the ParS Sequences for Integration.

For integration into the HML or MAT loci, the oligonucleotides G and H were used for PCR with pFG2 as template:

G: 5'-CTTCAAAGAAATATTTAAACTCATTATG-GCTTTTAGAGC ATATTACTCAGTGACACTATA-GAACGCGGCCGCCA-3' (SEQ ID NO: 16 in the appended sequence listing); and H: 5'-TCAGCGAGCAGAGAAGACAAGACATTTT-GTTTTACACCGG AGCCAAACTGTATAGGGAGAC-CGGCAGATCCGCGG-3' (SEQ ID NO: 17 in the appended sequence listing).

A mixture of Taq and Phusion (2/1 U) DNA polymerase was used for amplification of the ParS-NAT sequences in 100 µl of buffer 1× Go Taq, 2% DMSO, 200 µM dNTP, 1 µM of each primer.

The PCR reaction was performed as follows: 98° C. 2 min, 35 cycles at 98° C. 30 sec, 54° C. 30 sec, 72° C. 2.5 min followed by a period of 10 min at 72° C. The amplification products were then purified using a PCR Quiagen purification kit. 5 µg were used to transform a strain of wild-type yeast of W303 genetic background.

I.4. Integration of the ParS-NAT Sequences

The yeast cells were transformed following the protocol described by Gietz et al. (Gietz & Schiestl, 1991). After transformation, the cells were spread over YPD plates for 18 h to allow expression of the NAT marker. The cells were replicated on YPD plates containing Nourseothricin at a final concentration of 200 µg/ml.

After two NAT selection steps, resistant clones were selected for genomic DNA extraction and the integration of the ParS sequences was verified by PCR. The clones having proper integration were then transformed by pFG7 and placed in culture in minimal medium to perform microscopy on the living cells.

For integration into MAT, a YIL11 strain containing an operator/YFP-repressor at position 197 kb upstream of MAT was used to integrate a ParS-c2 sequence at 100 nt from the cleavage site of the HO endonuclease. The cells were then transformed with a plasmid carrying an inducible version of HO endonuclease and with pCM189 ParB-c2-mCherry.

I.5. Transfection of the HeLa Cells.

$5^{th}$ passage HeLa cells (ATCC) were seeded in 6-well dishes at a concentration of 400000 cells/well in 2 ml of DMEM medium, 10% foetal calf serum (FCS), 1× sodium pyruvate.

The cells proliferated for 24 h at 3TC, 5% $CO_2$. At 70% confluence, transfection was carried out. In short, 100 µl of OPTI-MEM® containing 1.5 µg of each plasmid and 10 µl of FUGENE® HD (Roche) transfection reagent were mixed together and liposome creation was conducted for 20 min at ambient temperature. The transfection mixture was then added drop-wise to the cells.

Under the experimental conditions used, a post-transfection incubation period of 20 h is sufficient to obtain a good fluorescence signal.

I.6. Transfection of the HeLa Cells.

$8^{th}$ passage Hela cells were seeded in 100 mm dishes at a concentration of $2.5 \ 10^6$ cells in 10 ml of DMEM medium, 10% FCS, 1X sodium pyruvate. 500 µl of OPTI-MEM® containing 15 µg of each PCR product to be integrated and 33.3 µl of FUGENE® HD (Roche) transfection reagent were mixed together and liposome creation was conducted for 20 min at ambient temperature. The transfection mixture was then added drop-wise to the cells.

5 h post-transfection, bleomycin sulfate was added for 20 h at a concentration of 0.1 µM. 20 h after the addition of bleomycin, the cells were washed twice in PBS then 10 ml of medium containing 200 µg/ml hygromycin was added. The cells were incubated for several days changing the medium every 3 days until non-transfected control cells were all counter-selected.

The resistant clones were then concentrated by successive passing on dishes of 35 mm, 60 mm, 100 mm and 140 mm, then frozen. The stable clones were seeded in 6-well dishes at a concentration of 400000 cells/well in 2 ml of DMEM medium, 10% FCS, 1X sodium pyruvate. The cells were grown for 24 h at 3TC, 5% $CO_2$. At 70% confluence, transfection was carried out. In short, 100 µl of OPTI-MEM® containing 1.5 µg of each plasmid and 10 µl of FUGENE® HD (Roche) transfection agent were mixed together and liposome creation was performed for 20 min at ambient temperature. The transfection mixture was then added drop-wise to the cells. Imaging of the ParB foci was performed 24 h post-transfection.

I.7. Image Acquisition.

For the yeasts, the cells were placed in culture until they reached mid-exponential growth phase in selective YNBD medium.

The images were acquired using an Olympus IX-81 inverted fluorescence microscope equipped with a COOL-SNAP™HQ camera (Princeton Instrument) and 100X PL APO NA 1.4 lens. The exposure time for ParB-c2-mCherry was 1000 ms. Acquisition on the cells was performed by real-time sequential acquisition (one image per second for 50 sec).

The images of human cells were acquired on a Nikon T5100 inverted fluorescence microscope fitted with a 40×PL APO NA 0.95 lens and Hamamatsu camera. The acquisition times were between 400 ms and 1000 ms.

I.8. Measurement of Particle Dynamics

The stacks of images were imported into the Image J software (rsbweb.nih.gov/ij/) and the position of the particles was determined automatically as a function of time using the Particle detector and tracker plug-in with the following parameter settings: Radius=4, CutOff=0, percentile 0.1, link=2, displacement=8.

The trajectories generated were visually inspected to verify the precision of particle tracking. The mean squared displacement (MSD) and velocity were calculated mathematically using the formulas:

$$\left\| \vec{V} \right\| = \sqrt{(x_i - x_{i-1})^2 + (y_i - y_{i-1})^2}$$

$$MSD = \sum_{0-i} \left[ \sqrt{(x_i - x_0)^2 + (y_i - y_0)^2} - \sqrt{(x_{i-1} - x_0)^2 + (y_{i-1} - y_0)^2} \right]^2$$

II. Results.

II.1. Generated Constructs.

A. Prior Remarks.

The DNA sequence used corresponded to the endogenous ParS-c2 and ParS-c3 sites respectively present in chromosomes 2 and 3 of Bcc. Each ParS sequence contains four binding sites of ParB proteins (i.e. recognition sites).

The selectable markers available for the integration of these sequences were the genes resistant to nourseothricin and hygromycin for the yeast cells and the gene resistant to hygromycin for the mammalian cells.

The ParS integration sequences are easily produced by PCR. This amplification allows targeted integration into the yeast cells and random integration into the mammalian cells.

A nucleic acid was also provided which encodes a fusion protein. This construct contains the sequence coding for either ParB-c2 or ParB-c3 fused to a fluorescent reporter, or GFP or its variant mCherry.

These nucleic acids were cloned in expression vectors specific to yeast or mammal.

For yeasts, the vectors were derivatives of the plasmids pCM184 and pCM189 which contain Tet OFF promoters allowing regulation of the expression of the sequence inserted downstream via the addition of doxycyclin (Belli et al, 1998; Gari et al, 1997). In the absence of doxycyclin, the expression of the construct is maximal.

For the mammalian cells, the vector was derived from the peGFP-c2 plasmid of Clontech© (GenBank Accession #: U57606). This plasmid contains a CMV promoter which leads to strong expression of the fusion protein in time-dependent manner. The ParB fusions do not contain any intracellular localization signal, but on account of their small size (<70 kDa) they freely diffuse within the cellular and nuclear volume.

B. For Use in Yeast

Figure 2:
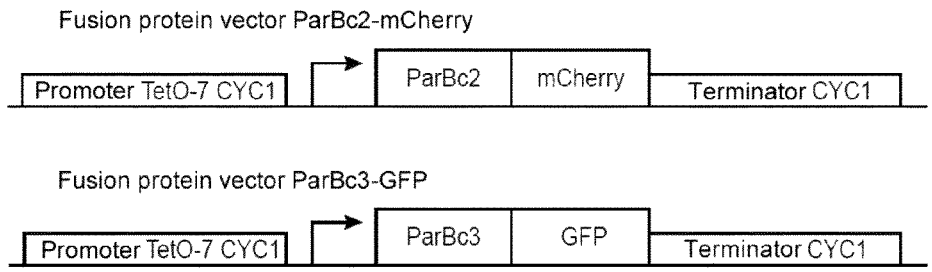
FIG. 2 is a schematic of the vectors containing the ParB fusions for expression in yeasts.

The two constructs ParB-c2-mCherry and ParB-c3-GFP used in the yeast are under the control of the CYC1-TetO-7 promoter (FIG. 2). This promoter contains seven TeT-Operators which are specifically bound by a transcriptional Transactivator (tTA) encoded on the same plasmid. The addition of doxycyclin induces repressing of the expression of the construct in dose-dependent manner.

Figure 3:
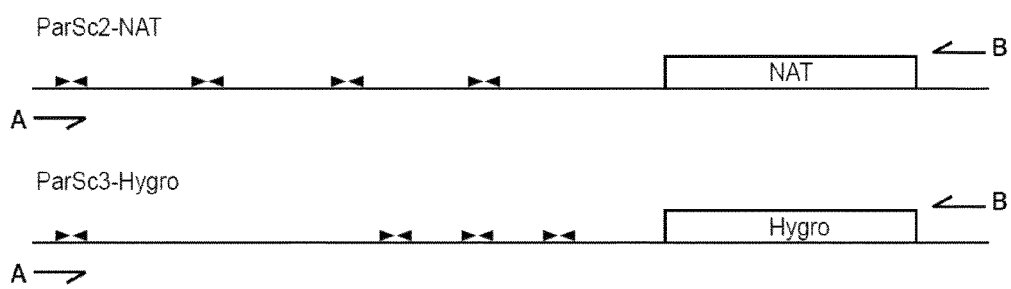
FIG. 3 is a schematic of the centromeric sequences ParS-c2 and ParS-c3.

The ParS sequences (FIG. 3) were inserted in the genomic DNA via PCR amplification using the following primer pairs A and B:

A: 5'-GTGACACTATAGAACGCGGCCGCCA-3' (SEQ ID NO: 18 in the appended sequence listing); and B: 5'-TATAGGGAGACCGGCAGATCCGCGG-3' (SEQ ID NO: 19 in the appended sequence listing).

These primers may contain sequences having homology with the sequences close to the target locus. This homology allows site specific integration of the ParS sequences using homologous recombination in the yeast.

Vectors containing Lox sites, flanking the region containing the selectable marker, can be used to restore auxotrophy for the selectable marker and thereby reduce insertion size to a minimum.

ParB-c2-mCherry, ParB-c3-GFP, ParS-c2 and ParS-c3 are associated with the markers URA3, TRP1, NAT and HYGRO, respectively. These four constructs can be used simultaneously.

C. For Use in Mammalian Cells.

Figure 4:
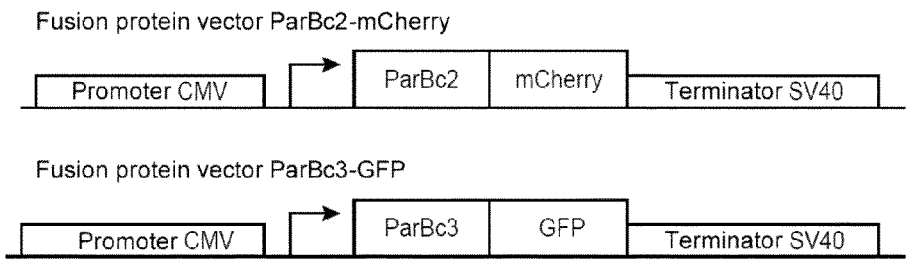
FIG. 4 is the schematic of the expression vectors of the ParB fusion proteins in mammalian cells.

For mammalian cells, the two constructs ParB-c2-mCherry and ParB-c3-GFP are under the control of the CMV promoter present in the backbone of the peGFP-c2 plasmid (FIG. 4). On this account, the expression of ParB is time-dependent. In the event of double tagging, peGFP-c2 ParB-c2-mCherry and ParB-c3-GFP must be transiently transfected.

The ParS sequences were amplified for integration by PCR using the following primer pairs C and D:

C: 5'-TCCAGCCCTCACTCCTTCTCTAGGCGCCGGAA-3' (SEQ ID NO: 20 in the appended sequence listing); and D: 5'-GTTCTCCAACTTCAAGAAACTGTTACCCAT-3' (SEQ ID NO: 21 in the appended sequence listing).

Figure 5:
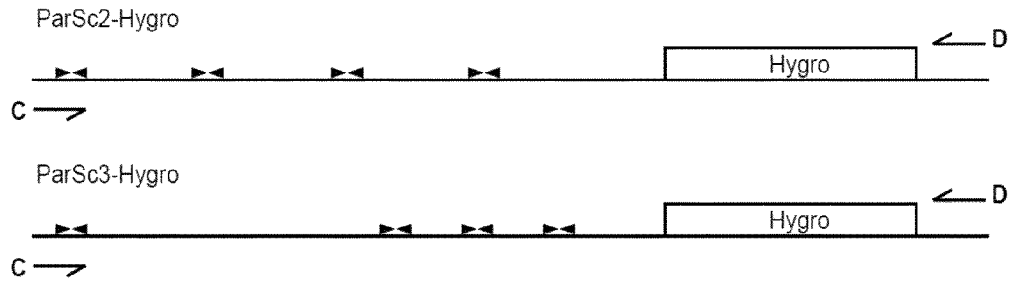
FIG. 5 is the schematic of the ParS-c2 and ParS-c3 centrometric sequences for integration into mammalian cells.

The PCR products were then transfected in the cells and the clones resistant to hygromycin were selected (FIG. 5). The insertion sites can then be determined using published techniques (Ozawa et al, 2004).

II.2. Detection of ParS Sequences In Vivo in Yeasts and Human Cells.

Figure 6:
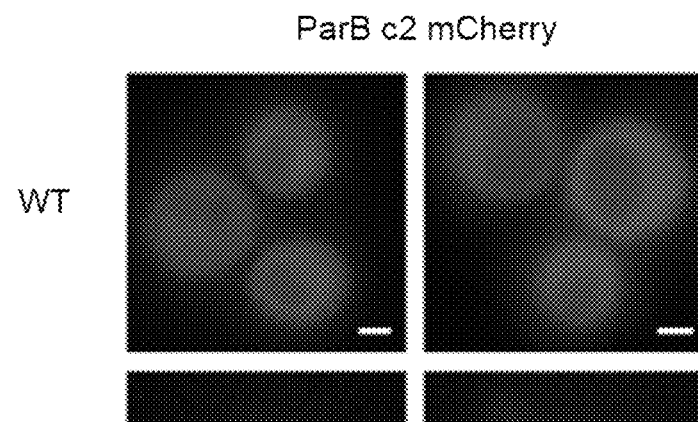
FIG. 6 gives photographs of yeast cells expressing the construct pCM189 ParB-c2-mCherry with the ParS-c2 construct whether inserted in the genome (ParS-c2) or not (WT).

A. In Yeast Cells (FIG. 6).

In non-labelled wild-type cells (WT), a diffuse fluorescent signal is visualised throughout the entire cell with the exception of the vacuole.

When the ParS-c2 construct is inserted in the genome (here the HML locus), a bright fluorescent dot induced by the binding of ParB on ParS can be seen (head of arrow). Bars: 2 μm.

Figure 7:
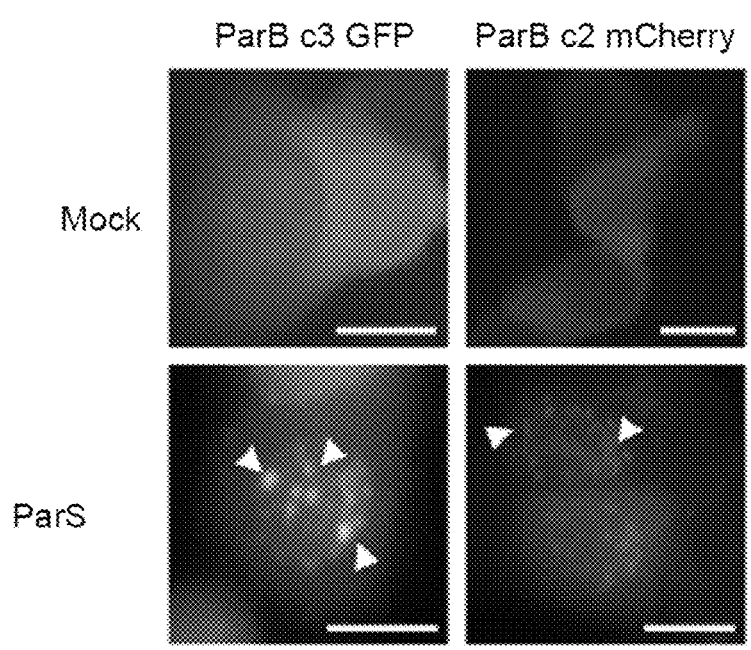
FIG. 7 gives photographs of human HeLa cells transiently expressing either the construct peGFP-c2 ParB-c3-GFP or peGFP-c2 ParB-c2-mCherry and co-transfected with water (Mock) or with a plasmid containing the sequences ParS-c2 or ParS-c3 (ParS). Bars 15 µm.

B. In Mammalian Cells with Plasmid ParS (FIG. 7).

Human HeLa cells transiently expressing either the peGFP-c2 ParB-c3-GFP construct or peGFP-c2 ParB-c2-mCherry were co-transfected with the plasmid containing the ParS-c2 or ParS-c3 (ParS) sequences. In this case, multiple fluorescent foci can be visualised concomitant with the fact that a high number of plasmid DNA molecules enter the cells during transfection (Batard et al, 2001).

No fluorescence focus was visible in the human HeLa cells transiently expressing either the peGFP-c2 ParB-c3-GFP construct, or the peGFP-c2 ParB-c2-mCherry construct which were co-transfected with water (Mock). Bars 15 μm.

Figure 8:
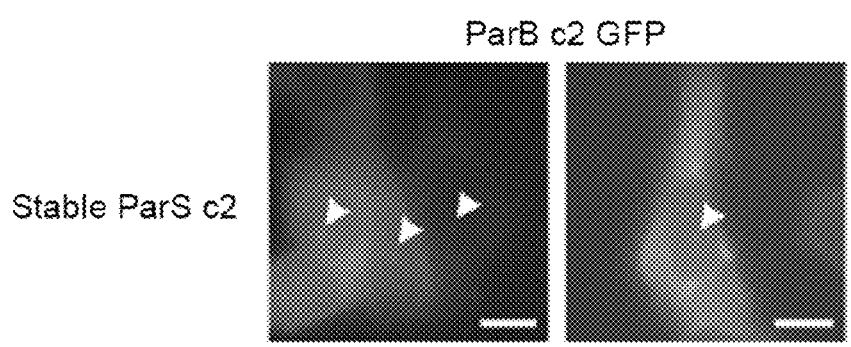
FIG. 8 gives photographs of human HeLa cells having stably integrated a single ParS-c2 construct and transiently expressing ParB-mcherry from the plasmid pFG9.

C. In Mammalian Cells with Stably Integrated ParS (FIG. 8).

In a HeLa cell line having stably integrated a single ParS-c2 construct and transiently expressing the peGFP-c2 ParB-c2-GFP construct, a fluorescence focus could be observed (arrow head).

II.3. Analysis of the Dynamics of the HML Locus.

This analysis was conducted using the ParS-c2/ParB-c2-mCherry localization system. The ParS-c2 sequence is integrated in the HML locus and the cells express the pCM189 ParB-c2-mCherry construct.

The position of the mCherry focus therefore corresponds to the position of the HML locus in vivo. The images were taken at an interval of 1 sec for 50 sec (FIG. 9).

The stacks of images derived from the acquisitions were imported into Image J software (rsbweb.nih.gov/ij/) and the position of the HML focus was monitored automatically over time.

The HML pathway (light coloured) during acquisition is given in FIG. 10A. FIG. 10B shows the characterization of HML movement by Mean-Square displacement (MSD) analysis. HML takes on a slow diffusive movement. The mean velocities and the calculated coefficients of diffusion are of the same order of magnitude as the values previously published (Bystricky et al, 2005; Bystricky et al, 2009).

II.4. Degradation of the ParS Sequence when Inducing a Single Double-Strand Break.

Cells having integrated the ParS-c2 construct at the MAT locus, at about 100 nucleotides away from the cleavage site corresponding to a single double-strand break with the HO endonuclease, express the pCM189 ParB-c2-mCherry construct.

Figure 11:
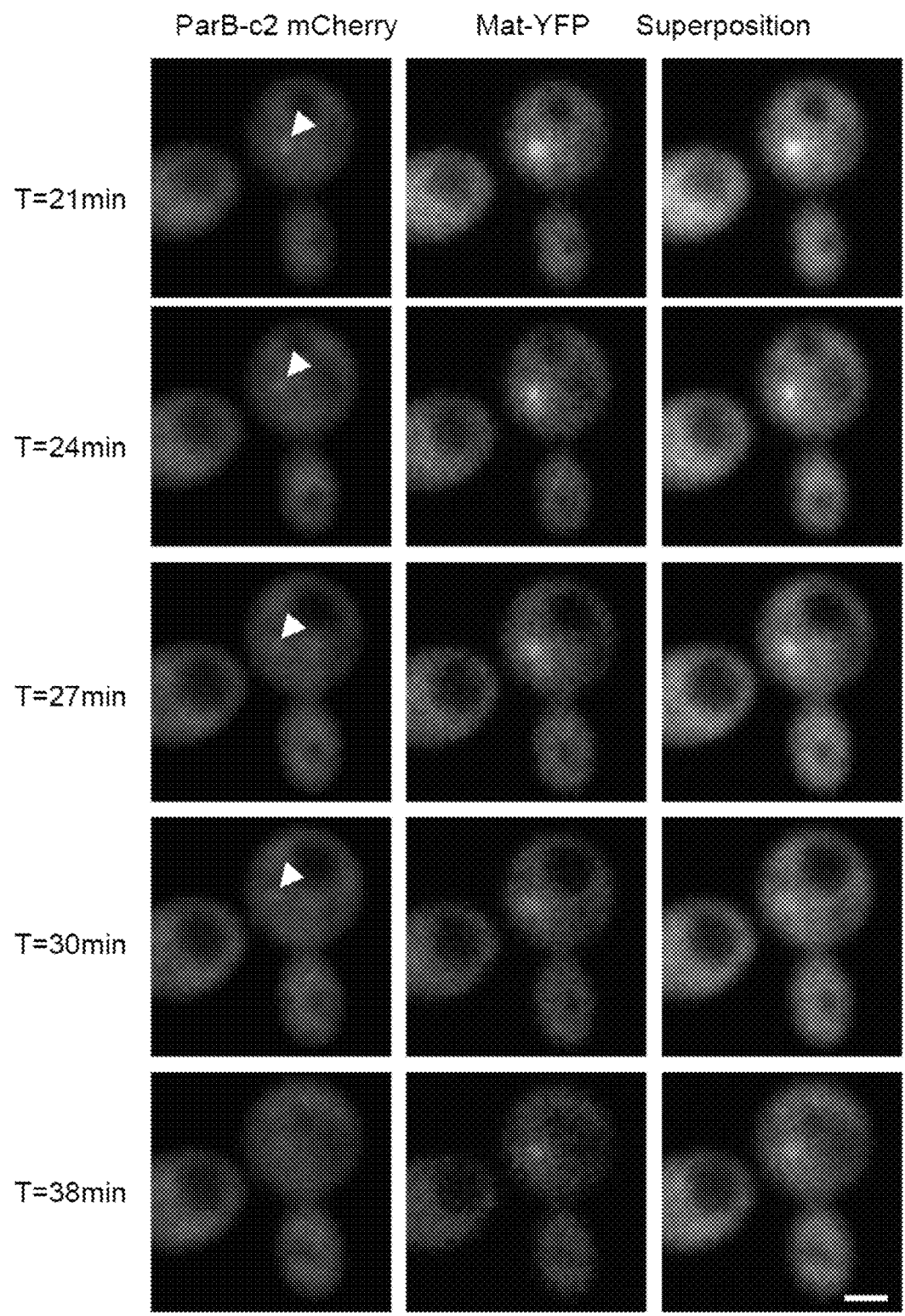
FIG. 11 shows the degradation of the ParS-c2 sequence inserted in the MAT locus when inducing a single double-strand break via the HO endonuclease. The ParS-c2 sequence is monitored by ParB-c2-mCherry (ParB-c2-mCherry) and the MAT locus is monitored (Mat-YFP). Bars 2 µm.

The cells were placed in culture in selective medium containing raffinose and inducing of the HO endonuclease was obtained by adding galactose (pGal-Ho). The cells were imaged in multicolour under an ANDOR Revolution rapid confocal microscope equipped with a YOKOGAWA CSU22 head and Andor iXonEM+DU888 camera. The images were taken with an Olympus PlanSApo 100× 1.40 lens. The position of the MAT locus carrying a lacO label at a distance of 4 kb (197 kb away from the left telomere of chromosome 3) was simultaneously monitored (FIG. 11).

The disappearance of the ParS foci corresponds to degradation of the sequences of the MAT locus in the vicinity of the HO cleavage site.

Figure 12:
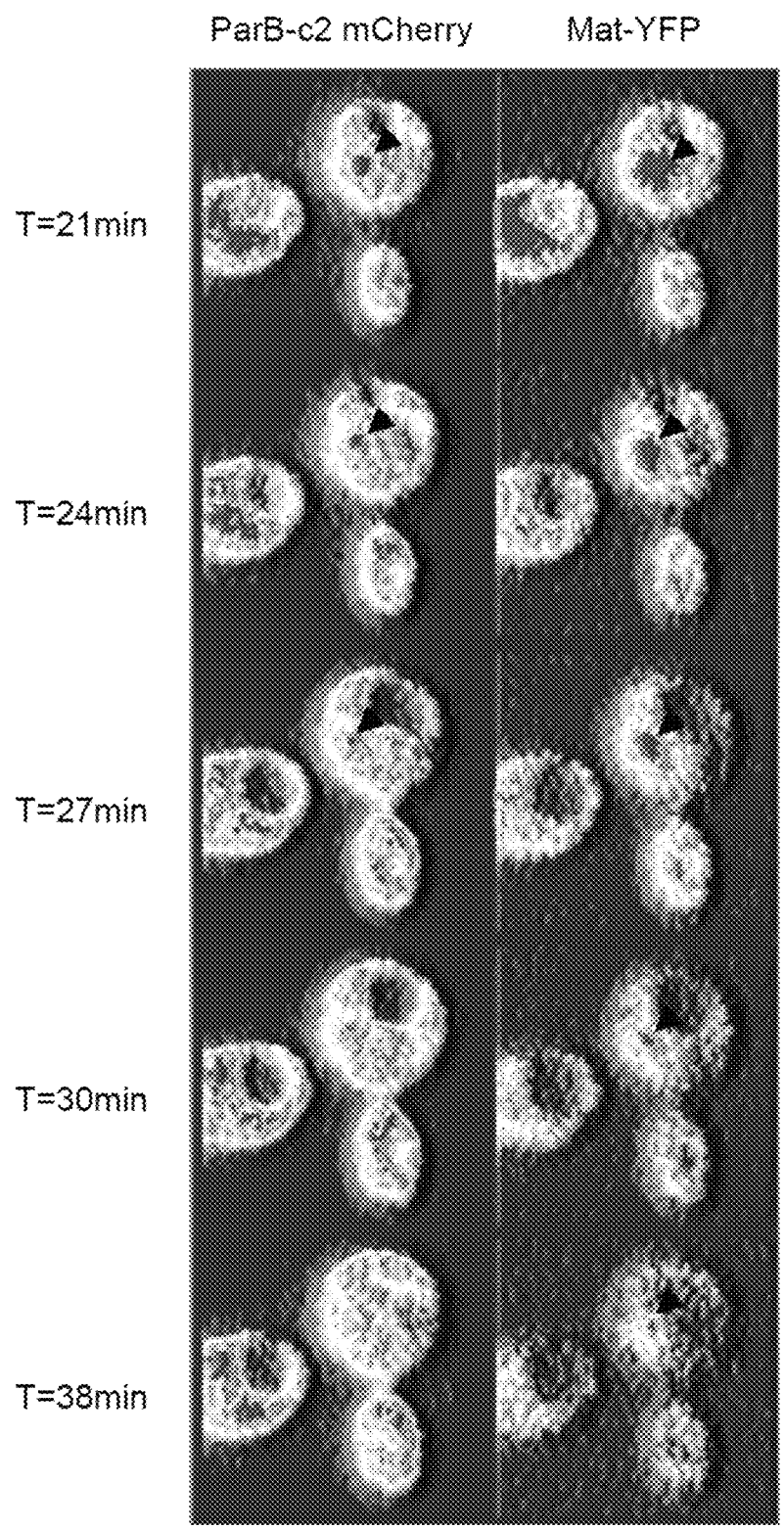
FIG. 12 illustrates quantification of the fluorescence signal of the cells shown in FIG. 11.

The images were imported into the Image J software and fluorescence, converted to arbitrary units, is illustrated in 3 dimensions (FIG. 12). The position of the YFP and mCherry foci is indicated by black arrow heads.

The disappearance of the mCherry focus is visible after 30 min. The loss of the focus is specific since the total fluorescence levels of mCherry are substantially identical throughout acquisition, in particular in the bud.

REFERENCES

Batard P, Jordan M, Wurm F (2001) Transfer of high copy number plasmid into mammalian cells by calcium phosphate transfection. Gene 270(1-2): 61-68
Belli G, Gari E, Piedrafita L, Aldea M, Herrero E (1998) An activator/repressor dual system allows tight tetracycline-regulated gene expression in budding yeast. Nucleic Acids Res 26(4): 942-947
Belmont A S (2001) Visualizing chromosome dynamics with GFP. Trends Cell Biol 11(6): 250-257
Belmont A S, Straight A F (1998) In vivo visualization of chromosomes using lac operator-repressor binding. Trends Cell Biol 8(3): 121-124
Bystricky K, Laroche T, van Houwe G, Blaszczyk M, Gasser S M (2005) Chromosome looping in yeast: telomere pairing and coordinated movement reflect anchoring efficiency and territorial organization. J Cell Biol 168(3): 375-387
Bystricky K, Van Attikum H, Montiel M D, Dion V, Gehlen L, Gasser S M (2009) Regulation of nuclear positioning and dynamics of the silent mating type loci by the yeast Ku70/Ku80 complex. Mol Cell Biol 29(3): 835-848
Dubarry N, Pasta F, Lane D (2006) ParABS systems of the four replicons of *Burkholderia cenocepacia*: new chromosome centromeres confer partition specificity. J Bacteriol 188(4): 1489-1496
Gari E, Piedrafita L, Aldea M, Herrero E (1997) A set of vectors with a tetracycline-regulatable promoter system for modulated gene expression in *Saccharomyces cerevisiae*. Yeast 13(9): 837-848
Gietz R D, Schiestl R H (1991) Applications of high efficiency lithium acetate transformation of intact yeast cells using single-stranded nucleic acids as carrier. Yeast 7(3): 253-263
Golovanov A P, Barilla D, Golovanova M, Hayes F, Lian L Y (2003) ParG, a protein required for active partition of bacterial plasmids, has a dimeric ribbon-helix-helix structure. Mol. Microbiol. 50: 1141-1153.
Li Y, Austin S (2002) The P1 plasmid is segregated to daughter cells by a 'capture and ejection' mechanism coordinated with *Escherichia coli* cell division. Mol Microbiol 46(1): 63-74
Lin D C, Grossman A D (1998) Identification and characterization of a bacterial chromosome partitioning site. Cell 92(5): 675-685
Livny J, Yamaichi Y, Waldor M K (2007) Distribution of centromere-like parS sites in bacteria: insights from comparative genomics. J Bacteriol 189(23): 8693-8703
Lynch A S, Wang J C (1995) sopB protein-mediated silencing of genes linked to the spoC locus of *Escherichia coli* F plasmid, Proc Natl Acad Sci USA 92(6): 1896-1900
Michaelis C, Ciosk R, Nasmyth K (1997) Cohesins: chromosomal proteins that prevent premature separation of sister chromatids. Cell 91(1): 35-45
Murray H, Ferreira H, Errington J (2006) The bacterial chromosome segregation protein Spo0J spreads along DNA from parS nucleation sites. Mol Microbiol 61(5): 1352-1361
Ozawa T, Itoyama T, Sadamori N, Yamada Y, Hata T, Tomonaga M, Isobe M (2004) Rapid isolation of viral integration site reveals frequent integration of HTLV-1 into expressed loci. J Hum Genet 49(3): 154-165
Straight A F, Belmont A S, Robinett C C, Murray A W (1996) GFP tagging of budding yeast chromosomes reveals that protein-protein interactions can mediate sister chromatid cohesion. Curr Biol 6(12): 1599-1608
Surtees J A, Funnell B E (1999) P1 ParB domain structure includes two independent multimerization domains. J. Bacteriol 181(19): 5898-5908
Therizols P, Duong T, Dujon B, Zimmer C, Fabre E Chromosome arm length and nuclear constraints determine the dynamic relationship of yeast subtelomeres. Proc Natl Acad Sci USA 107(5): 2025-2030

The invention claimed is:

1. A eukaryotic expression vector comprising a nucleotide sequence encoding a fusion protein comprising
a 1st polypeptide which is a DNA binding protein and which belongs to the partitioning system of bacterial DNA wherein the binding to DNA is solely dependent on the DNA binding protein belonging to the partitioning system of bacterial DNA used and on the recognition site at the DNA,
a derivative of a DNA binding protein belonging to the partitioning system of bacterial DNA or
a fragment of a DNA binding protein belonging to the partitioning system of bacterial DNA,
wherein the derivative of a DNA binding protein belonging to the partitioning system of bacterial DNA has at least 80% identity with the sequence of a DNA binding protein belonging to the partitioning system of bacterial DNA, contains at least the motif involved in DNA binding of the DNA binding protein belonging to the partitioning system of bacterial DNA, and is capable of specifically binding to DNA wherein the binding to DNA is solely dependent on the derivative used and on the recognition site at the DNA,
wherein the fragment of a DNA binding protein belonging to the partitioning system of bacterial DNA has one amino acid less at the C-terminal end and/or N-terminal end compared with the DNA binding protein belonging to the partitioning system of bacterial DNA and contains at least the motif involved in DNA binding of the DNA binding protein belonging to the partitioning system of bacterial DNA, and
wherein said DNA binding protein which belongs to the partitioning system of bacterial DNA is different from the ParB protein of the P1 plasmid of *E. coli*.

2. The vector according to claim 1, wherein the DNA binding protein belonging to the partitioning system of bacterial DNA is a ParB protein obtained from *Burkholderia cenocepacia*.

3. The vector according to claim 1, wherein the DNA binding protein belonging to the partitioning system of bacterial DNA is selected from the group consisting of:
the ParB protein encoded by chromosome 1 of Bcc designated ParB-c1;
the ParB protein encoded by chromosome 2 of Bcc designated ParB-c2;
the ParB protein encoded by chromosome 3 of Bcc designated ParB-c3;
the ParB protein encoded by the plasmid of Bcc designated ParB-p1, and a derivative of said ParB proteins or a fragment of said ParB proteins,
wherein the derivative of said ParB proteins has at least 80% identity with at least one of said ParB proteins, contains at least the motif involved in DNA binding of at least one of said ParB proteins, and is capable of specifically binding to DNA wherein the binding to DNA is solely dependent on the derivative used and on the recognition site at the DNA, and
wherein the fragment of said ParB proteins has one amino acid less at the C-terminal end and/or N-terminal end compared with at least one of said ParB proteins and contains at least the motif involved in DNA binding of at least one of said ParB proteins.

4. The vector according to claim 1, wherein said fusion protein comprises a 2nd polypeptide which is either a detectable polypeptide or a polypeptide involved in the regulation of gene expression.

5. The vector according to claim 4, wherein said detectable polypeptide is:
an enzyme capable of generating a detectable, optionally quantifiable signal; or
a bioluminescent or fluorescent polypeptide.

6. The vector according to claim 4, wherein said polypeptide involved in the regulation of gene expression is selected from the group consisting of a positive or negative transcription factor, a general transcription factor, a regulator of the expression of a promoter, a chromatin remodelling factor and a factor modifying the location of an adjacent gene.

7. The vector according to claim 1, said vector comprising, operationally linked, a promoter of eukaryotic type, a nucleotide sequence encoding a fusion protein and a eukaryotic transcription termination signal comprising a cleavage site and/or polyA signal.

8. An isolated polynucleotide selected from the group consisting of the different polynucleotides below:
i) a polynucleotide encoding a fusion protein comprising either:
the 1st polypeptide of claim 1; and
a 2nd polypeptide involved in the regulation of gene expression, or
the 1st polypeptide of claim 1, wherein the DNA binding protein belonging to the partitioning system of bacterial DNA is selected from the group consisting of:
the ParB protein encoded by chromosome 1 of Bcc designated ParB-c1; the ParB protein encoded by chromosome 2 of Bcc designated ParB-c2; the ParB protein encoded by chromosome 3 of Bcc designated ParB-c3; the ParB protein encoded by the plasmid of Bcc designated ParB-p1; and
a 2nd polypeptide that is detectable; and
ii) a polynucleotide complementary to the polynucleotide of item (i).

9. An isolated eukaryotic host organism transformed by or comprising a eukaryotic expression vector comprising a nucleotide sequence encoding a fusion protein comprising
a 1st polypeptide which is a DNA binding protein and which belongs to the partitioning system of bacterial DNA, wherein the binding to DNA is solely dependent on the DNA binding protein belonging to the partitioning system of bacterial DNA used and on the recognition site at the DNA,
a derivative of a DNA binding protein belonging to the partitioning system of bacterial DNA or
a fragment of a DNA binding protein belonging to the partitioning system of bacterial DNA,
wherein the derivative of a DNA binding protein belonging to the partitioning system of bacterial DNA has at least 80% identity with the sequence of a DNA binding protein belonging to the partitioning system of bacterial DNA, contains at least the motif involved in DNA binding of the DNA binding protein belonging to the partitioning system of bacterial DNA, and is capable of specifically binding to DNA wherein the binding to DNA is solely dependent on the derivative used and on the recognition site at the DNA,
wherein the fragment of a DNA binding protein belonging to the partitioning system of bacterial DNA has one amino acid less at the C-terminal end and/or N-terminal end compared with the DNA binding protein belonging to the partitioning system of bacterial DNA and contains at least the motif involved in DNA binding of the DNA binding protein belonging to the partitioning system of bacterial DNA, and wherein said DNA binding protein which belongs to the partitioning system of bacterial DNA is different from the ParB protein of the PI plasmid of *E. coli*.

10. The isolated eukaryotic host organism according to claim 9, wherein said organism is a micro-organism; an animal cell; a plant cell; a plant; or an animal with the exception of a human.

11. The isolated eukaryotic host organism according to claim 9, wherein said organism has integrated in its genome the nucleotide sequence having at least one recognition site recognised by a DNA binding protein belonging to the partitioning system of bacterial DNA, and expresses a fusion protein comprising the 1st polypeptide.

12. The isolated eukaryotic host organism according to claim 10, wherein the animal cell is an insect cell, a human cell, a hamster cell, a monkey cell, a rabbit cell, a mouse cell or a rat cell.

\* \* \* \* \*

UNITED STATES PATENT AND TRADEMARK OFFICE
CERTIFICATE OF CORRECTION

PATENT NO. : 9,611,486 B2
APPLICATION NO. : 14/006743
DATED : April 4, 2017
INVENTOR(S) : Kerstin Bystricky et al.

It is certified that error appears in the above-identified patent and that said Letters Patent is hereby corrected as shown below:

Column 11, Line 56: "H in the present invention" should be --in the present invention--.

Column 16, Line 60: "host organisms" should be --host organism--.

Column 47, Line 5: "PI plasmid" should be --P1 plasmid--.

Signed and Sealed this
Sixteenth Day of May, 2017

Michelle K. Lee
*Director of the United States Patent and Trademark Office*

SEQUENCE LISTING

<160> NUMBER OF SEQ ID NOS: 21

<210> SEQ ID NO 1
<211> LENGTH: 1062
<212> TYPE: DNA
<213> ORGANISM: Burkholderia cenocepacia
<220> FEATURE:
<221> NAME/KEY: CDS
<222> LOCATION: (1)..(1062)
<223> OTHER INFORMATION: Sequence coding for ParB protein carried by Bcc chromosome 2

<400> SEQUENCE: 1

```
atg aaa ccc tcc caa ttt gcc aaa gga ttc caa gcg cgc ccg gat atc      48
Met Lys Pro Ser Gln Phe Ala Lys Gly Phe Gln Ala Arg Pro Asp Ile
1               5                   10                  15 acg acg agc gag aag cgc acg gcg ctt gat cgg ctc aat gcg atc gac      96
Thr Thr Ser Glu Lys Arg Thr Ala Leu Asp Arg Leu Asn Ala Ile Asp
            20                  25                  30 ggc atc gtc aag tcc gag acg ccg acc ccg gcg ccg acc aaa tcc gcg     144
Gly Ile Val Lys Ser Glu Thr Pro Thr Pro Ala Pro Thr Lys Ser Ala
        35                  40                  45 aag aag gac atc gca ccg ccg cct gct ccg gaa ttc acg atc gat ccg     192
Lys Lys Asp Ile Ala Pro Pro Pro Ala Pro Glu Phe Thr Ile Asp Pro
    50                  55                  60 tcg atc gac gaa tcg cag caa tat cgc gcg tgg cgt ctc gag aat cgc     240
Ser Ile Asp Glu Ser Gln Gln Tyr Arg Ala Trp Arg Leu Glu Asn Arg
65                  70                  75                  80 tat gca ccc ggg cag gtg atc gag ctg ccg ctg aag gcg atc aag cac     288
Tyr Ala Pro Gly Gln Val Ile Glu Leu Pro Leu Lys Ala Ile Lys His
                85                  90                  95 agc ccg ttc aac ccg cgg cac ttc tat ctg aaa tcg tcg att gcc gaa     336
Ser Pro Phe Asn Pro Arg His Phe Tyr Leu Lys Ser Ser Ile Ala Glu
            100                 105                 110 ctc gcg gtc aac ctc gcg aag cag gga cag cag cag gcg atc cac gtg     384
Leu Ala Val Asn Leu Ala Lys Gln Gly Gln Gln Gln Ala Ile His Val
        115                 120                 125 att ccg gat tac gac aac ccg ggc acg tat ttc gtc agc gat ggc ggg     432
Ile Pro Asp Tyr Asp Asn Pro Gly Thr Tyr Phe Val Ser Asp Gly Gly
    130                 135                 140 cgt cgc gtg cgg gcg ctg aag gaa gcg aac aag gaa tcg gtc aag gcg     480
Arg Arg Val Arg Ala Leu Lys Glu Ala Asn Lys Glu Ser Val Lys Ala
145                 150                 155                 160 atc gtg atc gat gtg ccg atc ggc atc cag agc tac aag ctc ggc tac     528
Ile Val Ile Asp Val Pro Ile Gly Ile Gln Ser Tyr Lys Leu Gly Tyr
                165                 170                 175 gac ctg aac gtt cag cgc gat tcg cag acg gtg ttc gac aac gcc gtc     576
Asp Leu Asn Val Gln Arg Asp Ser Gln Thr Val Phe Asp Asn Ala Val
            180                 185                 190 gtg tgg cgc cgc ttc ctc gac gac aag cat ttc cag agc cag aaa gaa     624
Val Trp Arg Arg Phe Leu Asp Asp Lys His Phe Gln Ser Gln Lys Glu
        195                 200                 205 ctc tcc gag cat ctc ggc ctc gac gag tcg acg gtg gcc gtc gcg ctg     672
Leu Ser Glu His Leu Gly Leu Asp Glu Ser Thr Val Ala Val Ala Leu
    210                 215                 220 tcg atc ggc aag ttg ccg gaa gcg atc atg cag gaa atg gtc gca cgc     720
Ser Ile Gly Lys Leu Pro Glu Ala Ile Met Gln Glu Met Val Ala Arg
225                 230                 235                 240 ccc gat cgc ttc gga tcg aac atg gcg tat cag gtc ggc cgc tat cac     768
Pro Asp Arg Phe Gly Ser Asn Met Ala Tyr Gln Val Gly Arg Tyr His
                245                 250                 255
```

|  |  |  |  |  |  |  |  |  |  |  |  |  |  |  |  |
|---|---|---|---|---|---|---|---|---|---|---|---|---|---|---|---|
| aat | gcg | cgc | ggc | acc | gag | gcc | acg | ctg | cgg | ctg | atc | aac | aag | atc | gtg |
| Asn | Ala | Arg | Gly | Thr | Glu | Ala | Thr | Leu | Arg | Leu | Ile | Asn | Lys | Ile | Val |
|  |  |  | 260 |  |  |  | 265 |  |  |  | 270 |  |  |  |  |

816

|  |  |  |  |  |  |  |  |  |  |  |  |  |  |  |  |
|---|---|---|---|---|---|---|---|---|---|---|---|---|---|---|---|
| tcg | gac | gat | ctc | agc | acg | cgc | cag | gtg | tcg | gac | atc | gtc | aag | ggt | cgc |
| Ser | Asp | Asp | Leu | Ser | Thr | Arg | Gln | Val | Ser | Asp | Ile | Val | Lys | Gly | Arg |
|  |  | 275 |  |  |  |  | 280 |  |  |  |  | 285 |  |  |  |

864

|  |  |  |  |  |  |  |  |  |  |  |  |  |  |  |  |
|---|---|---|---|---|---|---|---|---|---|---|---|---|---|---|---|
| gtc | gcg | gca | cag | gag | acg | ccg | aag | cct | gcg | ggc | cgt | cag | cgc | tat | gcg |
| Val | Ala | Ala | Gln | Glu | Thr | Pro | Lys | Pro | Ala | Gly | Arg | Gln | Arg | Tyr | Ala |
|  | 290 |  |  |  |  | 295 |  |  |  |  | 300 |  |  |  |  |

912

|  |  |  |  |  |  |  |  |  |  |  |  |  |  |  |  |
|---|---|---|---|---|---|---|---|---|---|---|---|---|---|---|---|
| cag | cgt | ctc | gag | atc | aag | ctc | ggc | ggc | aag | tcg | gtc | ggc | gac | ctg | aag |
| Gln | Arg | Leu | Glu | Ile | Lys | Leu | Gly | Gly | Lys | Ser | Val | Gly | Asp | Leu | Lys |
| 305 |  |  |  | 310 |  |  |  |  | 315 |  |  |  |  | 320 |  |

960

|  |  |  |  |  |  |  |  |  |  |  |  |  |  |  |  |
|---|---|---|---|---|---|---|---|---|---|---|---|---|---|---|---|
| tcg | tat | ggc | gaa | gac | cgc | atc | gaa | ttg | cgc | ctg | cgc | ggc | ctc | ccg | aag |
| Ser | Tyr | Gly | Glu | Asp | Arg | Ile | Glu | Leu | Arg | Leu | Arg | Gly | Leu | Pro | Lys |
|  |  |  |  | 325 |  |  |  |  | 330 |  |  |  |  | 335 |  |

1008

|  |  |  |  |  |  |  |  |  |  |  |  |  |  |  |  |
|---|---|---|---|---|---|---|---|---|---|---|---|---|---|---|---|
| gac | aag | cgc | gac | gcg | att | ctc | gag | cag | ctc | gag | cgg | atg | ctg | ttg | tcg |
| Asp | Lys | Arg | Asp | Ala | Ile | Leu | Glu | Gln | Leu | Glu | Arg | Met | Leu | Leu | Ser |
|  |  |  | 340 |  |  |  |  | 345 |  |  |  |  | 350 |  |  |

1056

| gag | cat |
|---|---|
| Glu | His |

1062

<210> SEQ ID NO 2
<211> LENGTH: 354
<212> TYPE: PRT
<213> ORGANISM: Burkholderia cenocepacia

<400> SEQUENCE: 2

```
Met Lys Pro Ser Gln Phe Ala Lys Gly Phe Gln Ala Arg Pro Asp Ile
1               5                   10                  15

Thr Thr Ser Glu Lys Arg Thr Ala Leu Asp Arg Leu Asn Ala Ile Asp
            20                  25                  30

Gly Ile Val Lys Ser Glu Thr Pro Thr Pro Ala Pro Thr Lys Ser Ala
        35                  40                  45

Lys Lys Asp Ile Ala Pro Pro Pro Ala Pro Glu Phe Thr Ile Asp Pro
    50                  55                  60

Ser Ile Asp Glu Ser Gln Gln Tyr Arg Ala Trp Arg Leu Glu Asn Arg
65                  70                  75                  80

Tyr Ala Pro Gly Gln Val Ile Glu Leu Pro Leu Lys Ala Ile Lys His
                85                  90                  95

Ser Pro Phe Asn Pro Arg His Phe Tyr Leu Lys Ser Ser Ile Ala Glu
            100                 105                 110

Leu Ala Val Asn Leu Ala Lys Gln Gly Gln Gln Gln Ala Ile His Val
        115                 120                 125

Ile Pro Asp Tyr Asp Asn Pro Gly Thr Tyr Phe Val Ser Asp Gly Gly
    130                 135                 140

Arg Arg Val Arg Ala Leu Lys Glu Ala Asn Lys Glu Ser Val Lys Ala
145                 150                 155                 160

Ile Val Ile Asp Val Pro Ile Gly Ile Gln Ser Tyr Lys Leu Gly Tyr
                165                 170                 175

Asp Leu Asn Val Gln Arg Asp Ser Gln Thr Val Phe Asp Asn Ala Val
            180                 185                 190

Val Trp Arg Arg Phe Leu Asp Asp Lys His Phe Gln Ser Gln Lys Glu
        195                 200                 205

Leu Ser Glu His Leu Gly Leu Asp Glu Ser Thr Val Ala Val Ala Leu
    210                 215                 220

Ser Ile Gly Lys Leu Pro Glu Ala Ile Met Gln Glu Met Val Ala Arg
225                 230                 235                 240
```

```
Pro Asp Arg Phe Gly Ser Asn Met Ala Tyr Gln Val Gly Arg Tyr His
            245                 250                 255

Asn Ala Arg Gly Thr Glu Ala Thr Leu Arg Leu Ile Asn Lys Ile Val
        260                 265                 270

Ser Asp Asp Leu Ser Thr Arg Gln Val Ser Asp Ile Val Lys Gly Arg
            275                 280                 285

Val Ala Ala Gln Glu Thr Pro Lys Pro Ala Gly Arg Gln Arg Tyr Ala
        290                 295                 300

Gln Arg Leu Glu Ile Lys Leu Gly Gly Lys Ser Val Gly Asp Leu Lys
305                 310                 315                 320

Ser Tyr Gly Glu Asp Arg Ile Glu Leu Arg Leu Arg Gly Leu Pro Lys
                325                 330                 335

Asp Lys Arg Asp Ala Ile Leu Glu Gln Leu Glu Arg Met Leu Leu Ser
            340                 345                 350

Glu His

<210> SEQ ID NO 3
<211> LENGTH: 1032
<212> TYPE: DNA
<213> ORGANISM: Burkholderia cenocepacia
<220> FEATURE:
<221> NAME/KEY: CDS
<222> LOCATION: (1)..(1032)
<223> OTHER INFORMATION:

-continued

```
                165                 170                 175 tgg aaa cgt ctc ctc gac gag aag gtc ttt tcc gac cag aac acg ctg      576
Trp Lys Arg Leu Leu Asp Glu Lys Val Phe Ser Asp Gln Asn Thr Leu
            180                 185                 190 gcg gaa aaa atc ggc aag gac aag gcc tcg atc agc aag acg ctg tcg      624
Ala Glu Lys Ile Gly Lys Asp Lys Ala Ser Ile Ser Lys Thr Leu Ser
        195                 200                 205 ctc aac gcg ctg ccg aac acg ctg ctg gag cgg atg gcc agt gcg aac      672
Leu Asn Ala Leu Pro Asn Thr Leu Leu Glu Arg Met Ala Ser Ala Asn
    210                 215                 220 gac gtc gtc ggt ctg cag gcg gcg tac ttc ctc aaa ctg atc tat gaa      720
Asp Val Val Gly Leu Gln Ala Ala Tyr Phe Leu Lys Leu Ile Tyr Glu
225                 230                 235                 240 cgc ctg ggc gag ccg acg gcc gac cgg ctg ctg acg gcc gtg atc gac      768
Arg Leu Gly Glu Pro Thr Ala Asp Arg Leu Leu Thr Ala Val Ile Asp
                245                 250                 255 cgg aaa aaa tcc gtc cgc gat ctc gag aat ttc ctg cgt gcg cag agc      816
Arg Lys Lys Ser Val Arg Asp Leu Glu Asn Phe Leu Arg Ala Gln Ser
            260                 265                 270 gac ggc acc aag aag gcc gga cgc acg cgc tac agc gtt cgt cac gac      864
Asp Gly Thr Lys Lys Ala Gly Arg Thr Arg Tyr Ser Val Arg His Asp
        275                 280                 285 ttc gcg ctc gaa tcg cgc gcg atc ggc cag ttg aag acg tat ccg gac      912
Phe Ala Leu Glu Ser Arg Ala Ile Gly Gln Leu Lys Thr Tyr Pro Asp
    290                 295                 300 ggg cgt ctg gat ctg caa ctc aag ggc gtc gac gca tcc cac cag gaa      960
Gly Arg Leu Asp Leu Gln Leu Lys Gly Val Asp Ala Ser His Gln Glu
305                 310                 315                 320 gcg ctt gcc gac aag ctc aag acc gtc atc gac gcg tac gtg gcg gat     1008
Ala Leu Ala Asp Lys Leu Lys Thr Val Ile Asp Ala Tyr Val Ala Asp
                325                 330                 335 ctg gcg acg gcc acg tca aag cat                                     1032
Leu Ala Thr Ala Thr Ser Lys His
            340

<210> SEQ ID NO 4
<211> LENGTH: 344
<212> TYPE: PRT
<213> ORGANISM: Burkholderia cenocepacia

<400> SEQUENCE: 4

Met Ala Lys Asp Thr Ser Lys Asp Lys Lys Pro Thr Gly Asn Leu His
1               5                   10                  15

Leu Ala Ala Gly Leu Leu Arg Gly Leu Ala Gln Glu Asn Ala Ala Leu
            20                  25                  30

Glu Thr Arg Leu Pro Glu Pro Thr Ala Ala Pro Ala Ala Val Val Glu
        35                  40                  45

Ala Thr Pro Ala Ser Ala Pro Ala Ala Ala Thr Pro Ala Gly Thr Ala
    50                  55                  60

Asp Leu Gly Ala Pro Gln Lys Val Leu Val Lys Asp Cys Ile Pro Asn
65                  70                  75                  80

Pro Phe Asn Pro Arg Val Phe Tyr Ser Glu Ser Ser Leu His Glu Leu
                85                  90                  95

Ala Leu Thr Leu Lys Arg Glu Gly Gln Ile Glu Pro Ile Lys Val Thr
            100                 105                 110

Arg Leu Pro Glu Phe Pro Gly Lys Leu Val Val Ile Asp Gly Gln Arg
        115                 120                 125

Arg Leu Arg Ala Thr Ser Ile Asn Gly Asp Glu Thr Ile Asn Ala Thr

```
            130                 135                 140
Phe Arg Thr Asp His Thr Pro Glu Gln Leu Tyr Thr Ile Ala Tyr Arg
145                 150                 155                 160

Ala Asn His Asp His Glu Arg Gln Thr Ile Phe Asp Asp Ala Val Ala
                165                 170                 175

Trp Lys Arg Leu Leu Asp Glu Lys Val Phe Ser Asp Gln Asn Thr Leu
                180                 185                 190

Ala Glu Lys Ile Gly Lys Asp Lys Ala Ser Ile Ser Lys Thr Leu Ser
                195                 200                 205

Leu Asn Ala Leu Pro Asn Thr Leu Leu Glu Arg Met Ala Ser Ala Asn
            210                 215                 220

Asp Val Val Gly Leu Gln Ala Ala Tyr Phe Leu Lys Leu Ile Tyr Glu
225                 230                 235                 240

Arg Leu Gly Glu Pro Thr Ala Asp Arg Leu Leu Thr Ala Val Ile Asp
                245                 250                 255

Arg Lys Lys Ser Val Arg Asp Leu Glu Asn Phe Leu Arg Ala Gln Ser
                260                 265                 270

Asp Gly Thr Lys Lys Ala Gly Arg Thr Arg Tyr Ser Val Arg His Asp
                275                 280                 285

Phe Ala Leu Glu Ser Arg Ala Ile Gly Gln Leu Lys Thr Tyr Pro Asp
    290                 295                 300

Gly Arg Leu Asp Leu Gln Leu Lys Gly Val Asp Ala Ser His Gln Glu
305                 310                 315                 320

Ala Leu Ala Asp Lys Leu Lys Thr Val Ile Asp Ala Tyr Val Ala Asp
                325                 330                 335

Leu Ala Thr Ala Thr Ser Lys His
            340

<210> SEQ ID NO 5
<211> LENGTH: 16
<212> TYPE: DNA
<213> ORGANISM: unknown
<220> FEATURE:
<223> OTHER INFORMATION: Recognition site recognised by the DNA binding
      protein belonging to the partitioning system of bacterial DNA
<220> FEATURE:
<221> NAME/KEY: misc_feature
<222> LOCATION: (1)..(2)
<223> OTHER INFORMATION: n represents a, g, c or t
<220> FEATURE:
<221> NAME/KEY: misc_feature
<222> LOCATION: (4)..(7)
<223> OTHER INFORMATION: n represents a, g, c or t
<220> FEATURE:
<221> NAME/KEY: misc_feature
<222> LOCATION: (10)..(13)
<223> OTHER INFORMATION: n represents a, g, c or t
<220> FEATURE:
<221> NAME/KEY: misc_feature
<222> LOCATION: (15)..(16)
<223> OTHER INFORMATION: n represents a, g, c or t

<400> SEQUENCE: 5
nntnnnncgn nnnann                                                    16

<210> SEQ ID NO 6
<211> LENGTH: 16
<212> TYPE: DNA
<213> ORGANISM: unknown
<220> FEATURE:
<223> OTHER INFORMATION: Recognition site recognised by the DNA binding
      protein belonging to the partitioning system of bacterial DNA
<220> FEATURE:
```

```
<221> NAME/KEY: misc_feature
<222> LOCATION: (1)..(1)
<223> OTHER INFORMATION: n represents g, c or t
<220> FEATURE:
<221> NAME/KEY: misc_feature
<222> LOCATION: (4)..(4)
<223> OTHER INFORMATION: n represents t or g
<220> FEATURE:
<221> NAME/KEY: misc_feature
<222> LOCATION: (5)..(5)
<223> OTHER INFORMATION: n represents a or t
<220> FEATURE:
<221> NAME/KEY: misc_feature
<222> LOCATION: (6)..(6)
<223> OTHER INFORMATION: n represents t or c
<220> FEATURE:
<221> NAME/KEY: misc_feature
<222> LOCATION: (7)..(7)
<223> OTHER INFORMATION: n represents g or a
<220> FEATURE:
<221> NAME/KEY: misc_feature
<222> LOCATION: (10)..(10)
<223> OTHER INFORMATION: n represents t or c
<220> FEATURE:
<221> NAME/KEY: misc_feature
<222> LOCATION: (11)..(11)
<223> OTHER INFORMATION: n represents g or a
<220> FEATURE:
<221> NAME/KEY: misc_feature
<222> LOCATION: (12)..(12)
<223> OTHER INFORMATION: n represents a or t
<220> FEATURE:
<221> NAME/KEY: misc_feature
<222> LOCATION: (13)..(13)
<223> OTHER INFORMATION: n represents a or c

<400> SEQUENCE: 6
nttnnnncgn nnnaac                                                 16

<210> SEQ ID NO 7
<211> LENGTH: 16
<212> TYPE: DNA
<213> ORGANISM: Burkholderia cenocepacia
<220> FEATURE:
<221> NAME/KEY: protein_bind
<222> LOCATION: (1)..(16)
<223> OTHER INFORMATION: Recognition site by ParB belonging to ParS-c2

<400> SEQUENCE: 7
gtttatgcgc ataaac                                                 16

<210> SEQ ID NO 8
<211> LENGTH: 16
<212> TYPE: DNA
<213> ORGANISM: Burkholderia cenocepacia
<220> FEATURE:
<221> NAME/KEY: protein_bind
<222> LOCATION: (1)..(16)
<223> OTHER INFORMATION: Recognition site by ParB belonging to ParS-c2

<400> SEQUENCE: 8
ctttatgcgc ataaac                                                 16

<210> SEQ ID NO 9
<211> LENGTH: 16
<212> TYPE: DNA
<213> ORGANISM: Burkholderia cenocepacia
<220> FEATURE:
<221> NAME/KEY: protein_bind
<222> LOCATION: (1)..(16)
<223> OTHER INFORMATION: Recognition site by ParB belonging to ParS-c3

<400> SEQUENCE: 9
```

```
gttgtcacgt gacaac                                                          16
```

<210> SEQ ID NO 10
<211> LENGTH: 16
<212> TYPE: DNA
<213> ORGANISM: Burkholderia cenocepacia
<220> FEATURE:
<221> NAME/KEY: protein_bind
<222> LOCATION: (1)..(10)
<223> OTHER INFORMATION: Recognition site by ParB belonging to ParS-c3

<400> SEQUENCE: 10

```
tttgtcacgt gacaac                                                          16
```

<210> SEQ ID NO 11
<211> LENGTH: 16
<212> TYPE: DNA
<213> ORGANISM: Burkholderia cenocepacia
<220> FEATURE:
<221> NAME/KEY: protein_bind
<222> LOCATION: (1)..(16)
<223> OTHER INFORMATION: Recognition site by ParB belonging to ParS-c3

<400> SEQUENCE: 11

```
cttgtcacgt gacaac                                                          16
```

<210> SEQ ID NO 12
<211> LENGTH: 1049
<212> TYPE: DNA
<213> ORGANISM: Burkholderia cenocepacia
<220> FEATURE:
<221> NAME/KEY: gene
<222> LOCATION: (1)..(1049)
<223> OTHER INFORMATION: ParS sequence carried by Bcc chromosome 2

<400> SEQUENCE: 12

```
cgtacgctgc aggtcgacgg atcccccat tcggacgatc ggtttatgcg cataaacgag           60
cggtggatgt tcgatggctc gtttggacgg tgtggtgaag aggaagcggc tgatgccgag         120
tgatcgatgc cctgctcagg attacgtctt catgggcgta tcgtcgggc cgttcgtggc          180
agagatatct cgacgctctc tcctttcgcg ggacgagccg cgttgcctgc gagccgcgag         240
tttgtgcgca taaagactgc ggaggccgat cgatgggctt cgtcgctaga gcgcatggta         300
ttcactcgcg agcgtccggc gtgagctgcg tgtcgtagtc aggtgcgtag atcacgaggt         360
gcgtcgttga atggacgtgc atggaggcaa tgtcctgccg ggccgtagtg tttatgcgca         420
taaaccagag gcaacgatag gccgcgacga agcgccgttg acagagacta cgcctgagtc         480
aggcgggcaa tgacgtcatg tcggggacga cggtctatcg atatagccat cgcgcagtgc         540
cgttgcgtgt cgacatatgt ccatgccacg agccacgctg tacctcgccc ggcaatcgcg         600
cgctttatgc gcataaacct agccggcgtg ttccgcaatc gcatacccct ttcgcgaccc         660
gagacagccc tcacgagaca gccctcacga gacagccctc acgagacagc cctcacgaga         720
catcggctgc gccggtcgtc ggccccgcga agccacccgc ccgactttat gcgcataaac         780
aaccactctt cgacgcgtcg ccgaacacag gacactcccc tctcgcgatc actgcgcatc         840
gccaaaccga aaccgcctca gcgacctatc aagaggaacc ccacaccgat ctcgattgcc         900
ccccatcagg cccctcgatg cagactcgct acaatacagg cctcacccct cctgccttga         960
acgatgatca cgatctacca caaccccga tgctcgaaat cccgcgagac gcttgcgttg        1020
gtcgagtcgc tgaataccgc cggcgcgcc                                         1049
```

<210> SEQ ID NO 13
<211> LENGTH: 1181
<212> TYPE: DNA
<213> ORGANISM: Burkholderia cenocepacia
<220> FEATURE:
<221> NAME/KEY: gene
<222> LOCATION: (1)..(1181)
<223> OTHER INFORMATION: ParS sequence carried by Bcc chromosome 3

<400> SEQUENCE: 13

```
ccggcgtcaa cttctatcta ctccgaatcc caccattcca tgaatcgcgc gaccgacgtg     60
tgcgttgtca cgtgacaact ggcgctaaat atcggtgcgc cccgtactcg attggaggct    120
caagggaatt caatggtaga gcaccgatcc tcccggctca tcggcggatc ccgcgaagaa    180
tcagccgaaa cgtatcaaaa acaacaaatc acatatcaat caaaacaaat ctagccgcag    240
ccgtatcaat cttcaatgcc cgggcgttga aaactcatac gcccctattt cccgagggtg    300
cagcatccgt tttgcgtgaa acagcatgaa gaatatggcg caaaccattg cccgacaagg    360
atttccgggc gagtgcttat tttcgggaaa tgtttcacga tccgacccgt ttgggttgtt    420
acatgcctct gacgtatgga ttcagcgcca gtagcagttc atacctgcgg ctatctccgg    480
catcaacagt ccaccagcgc aggcaccggc tggcggccac gaagcaacct accctatcgg    540
ccggcacgcg tggaaacgca gggtcgcgct cctataaatg gggacatatc atgacagccc    600
catgcagcct ttgcgacaga gctcggcagc attgcgtccg cccttgaggg tccgcacgcc    660
ggcaggaatt tggccgcgca accgatcgtg ccaaggcctt cgcagcccca agccgtttct    720
ttgcgacagc aacggggcgc tcctcgccat agagtcgcca tcgcttgaac ttcccggcat    780
cgcgtcctgt tgtcacgtga caactcaccg atggacacac ggacaaacca cctcggcgaa    840
aactatcaac ttcgtgcgtt tccccgacaa tatgcctcca cgccgcgagc gtcgaccagc    900
aacaactatt cttaactgac cacaaatccc ctatccgaga cagcaccttg ggattgtttg    960
tcacgtgaca actcatcttc ccaggtagac gtccgcgatt tagcgcccgt gtatcgataa   1020
ttagagtgaa gcgattaccc cgcgctccag gtcgcaatcg aaaactttcg ctcgacgtag   1080
cactcggagg aatcgatatc cggcgacttg tcacgtgaca accggctctt cctcgttacc   1140
ggggtctcag cgccccggat ttgggttaat taaggcgcgc c                       1181
```

<210> SEQ ID NO 14
<211> LENGTH: 28
<212> TYPE: DNA
<213> ORGANISM: unknown
<220> FEATURE:
<223> OTHER INFORMATION: Primer E

<400> SEQUENCE: 14

```
attagcggat cctacctgac gcttttta                                        28
```

<210> SEQ ID NO 15
<211> LENGTH: 34
<212> TYPE: DNA
<213> ORGANISM: unknown
<220> FEATURE:
<223> OTHER INFORMATION: Primer F

<400> SEQUENCE: 15

```
ggaattgcgg ccgcttactt gtacagctcg tcca                                 34
```

<210> SEQ ID NO 16
<211> LENGTH: 75

```
<212> TYPE: DNA
<213> ORGANISM: unknown
<220> FEATURE:
<223> OTHER INFORMATION: Oligonucleotide G

<400> SEQUENCE: 16
cttcaaagaa atatttaaac tcatttatgg cttttagagc atattactca gtgacactat    60
agaacgcggc cgcca                                                     75

<210> SEQ ID NO 17
<211> LENGTH: 75
<212> TYPE: DNA
<213> ORGANISM: Unknown
<220> FEATURE:
<223> OTHER INFORMATION: Oligonucleotide H

<400> SEQUENCE: 17
tcagcgagca gagaagacaa gacattttgt tttacaccgg agccaaactg tatagggaga    60
ccggcagatc cgcgg                                                     75

<210> SEQ ID NO 18
<211> LENGTH: 25
<212> TYPE: DNA
<213> ORGANISM: unknown
<220> FEATURE:
<223> OTHER INFORMATION: Primer A

<400> SEQUENCE: 18
gtgacactat agaacgcggc cgcca                                          25

<210> SEQ ID NO 19
<211> LENGTH: 25
<212> TYPE: DNA
<213> ORGANISM: unknown
<220> FEATURE:
<223> OTHER INFORMATION: Primer B

<400> SEQUENCE: 19
tatagggaga ccggcagatc cgcgg                                          25

<210> SEQ ID NO 20
<211> LENGTH: 32
<212> TYPE: DNA
<213> ORGANISM: unknown
<220> FEATURE:
<223> OTHER INFORMATION: Primer C

<400> SEQUENCE: 20
tccagccctc actccttctc taggcgccgg aa                                  32

<210> SEQ ID NO 21
<211> LENGTH: 30
<212> TYPE: DNA
<213> ORGANISM: unknown
<220> FEATURE:
<223> OTHER INFORMATION: Primer D

<400> SEQUENCE: 21
gttctccaac ttcaagaaac tgttacccat                                     30
```